(12) United States Patent
Stella et al.

(10) Patent No.: US 8,263,058 B2
(45) Date of Patent: Sep. 11, 2012

(54) PERSONAL CARE COMPOSITIONS THAT DEPOSIT HYDROPHILIC BENEFIT AGENTS

(75) Inventors: Qing Stella, Cincinnati, OH (US); Steven Hardy Page, Lawrenceburg, IN (US); Mark Leslie Kacher, Mason, OH (US); Karl Shiqing Wei, Mason, OH (US); Magda El-Nokaly, Cincinnati, OH (US)

(73) Assignee: The Procter & Gamble Company, Cincinnati, OH (US)

(*) Notice: Subject to any disclaimer, the term of this patent is extended or adjusted under 35 U.S.C. 154(b) by 894 days.

(21) Appl. No.: 11/894,142

(22) Filed: Aug. 20, 2007

(65) Prior Publication Data

US 2008/0031845 A1 Feb. 7, 2008

Related U.S. Application Data

(63) Continuation of application No. 11/103,254, filed on Apr. 11, 2005.

(60) Provisional application No. 60/564,259, filed on Apr. 21, 2004.

(51) Int. Cl.
A61K 31/74 (2006.01)
A61K 8/02 (2006.01)

(52) U.S. Cl. .................... 424/78.03; 424/401

(58) Field of Classification Search .......... 424/78.03, 424/401
See application file for complete search history.

(56) References Cited

U.S. PATENT DOCUMENTS

| | | |
|---|---|---|
| 3,929,678 A | 12/1975 | Laughlin et al. |
| 4,557,853 A | 12/1985 | Collins |
| 4,767,625 A | 8/1988 | Mitsuno et al. |
| 4,772,471 A | 9/1988 | Vanlerberghe et al. |
| 4,940,576 A | 7/1990 | Walsh |
| 4,975,218 A | 12/1990 | Rosser |
| 4,999,348 A | 3/1991 | Cioca et al. |
| 5,124,081 A | 6/1992 | Vanlerberghe et al. |
| 5,190,915 A | 3/1993 | Behan et al. |
| 5,215,757 A | 6/1993 | El-Nokaly |
| 5,229,104 A | 7/1993 | Sottery et al. |
| 5,372,814 A | 12/1994 | Mizushima et al. |
| 5,374,372 A | 12/1994 | Broze et al. |
| 5,429,820 A | 7/1995 | Kamitani et al. |
| 5,458,872 A | 10/1995 | Durand |
| 5,565,193 A | 10/1996 | Midha et al. |
| 5,599,555 A | 2/1997 | El-Nokaly |
| 5,622,694 A | 4/1997 | Torgerson et al. |
| 5,688,831 A * | 11/1997 | El-Nokaly et al. ............ 424/401 |
| 5,693,670 A | 12/1997 | Philippe et al. |
| 5,696,074 A | 12/1997 | Nickel et al. |
| 5,747,009 A | 5/1998 | Hansenne |
| 5,788,972 A | 8/1998 | De Salvert et al. |
| 5,912,002 A | 6/1999 | Grieveson et al. |
| 5,939,082 A | 8/1999 | Oblong et al. |
| 6,004,584 A | 12/1999 | Peterson et al. |
| 6,074,628 A | 6/2000 | Bolich, Jr. et al. |
| 6,149,900 A | 11/2000 | Afriat et al. |
| 6,231,837 B1 | 5/2001 | Stroud et al. |
| 6,277,360 B1 | 8/2001 | Carew et al. |
| 6,280,757 B1 | 8/2001 | McAtee et al. |
| 6,391,321 B1 | 5/2002 | Gers-Barlag et al. |
| 6,395,691 B1 | 5/2002 | Tsaur |
| 6,451,293 B1 | 9/2002 | Schreier et al. |
| 6,620,407 B1 | 9/2003 | Gers-Barlag et al. |
| 6,645,474 B1 | 11/2003 | Galdi et al. |
| 6,645,511 B2 | 11/2003 | Aronson et al. |
| 6,706,257 B1 | 3/2004 | McCook et al. |
| 6,797,683 B2 | 9/2004 | Shana'a et al. |
| 2002/0001605 A1 | 1/2002 | Carew et al. |
| 2002/0098230 A1 | 7/2002 | Nguyen et al. |
| 2002/0155080 A1 | 10/2002 | Glenn et al. |
| 2003/0082219 A1 | 5/2003 | Warren et al. |
| 2003/0161796 A1 | 8/2003 | Bracken et al. |
| 2003/0171231 A1 | 9/2003 | Shana'a et al. |
| 2003/0232030 A1 | 12/2003 | Lu et al. |
| 2004/0037793 A1 | 2/2004 | Nieendick et al. |
| 2004/0045101 A1 | 3/2004 | Miczewski et al. |
| 2004/0048757 A1 | 3/2004 | Zhang et al. |
| 2004/0048758 A1 | 3/2004 | Zhang et al. |
| 2004/0091446 A1 | 5/2004 | Massaro et al. |
| 2004/0234467 A1 * | 11/2004 | Ananthapadmanabhan et al. ............ 424/70.1 |
| 2004/0248748 A1 | 12/2004 | Wei et al. |
| 2005/0238595 A1 | 10/2005 | Stella et al. |

(Continued)

FOREIGN PATENT DOCUMENTS

EP 0466235 A1 1/1992

(Continued)

OTHER PUBLICATIONS

R. Inaba et al., J. of SCCJ (1995), 29(2), 146-53, Inventor Inaba, Assignee Nippon Shikizai, Inc. Application of porous starch complex powder (Abstract).
Suzuki et al., J. Soc. Cosmet. Chem. 43, 21 (1992), KAO, Oil/POE(20) octyldodecyl ether/glycerin bicontinous, 1) water in LC containing oily residue, 2) LC->O/LC->O/W. Sebum and oil-based cosmetics. Cleansing, remove oily makeup.
K. Yahagi, J. Soc. Cosmet. Chem. 43, 275, (1992), KAO, Dimethicone copolyol LC. Optimum HLB is 4, 100ug Si/g hair. Hair conditioning and softening.
Lyotropic Liquid Crystals Stig Friberg (Ed.), American Chemical Society, Washington, D.C., 1976, pp. 13-27.
Encyclopedia of Polymers and Thickeners, Cosmetic and Toiletries, p. 95, vol. 108, May 1993.
Van Nostrand Reinhold's Encyclopedia of Chemistry, 4th Edition, pp. 155, 169, 556 and 849 (1984).

Primary Examiner — Fereydoun G Sajjadi
Assistant Examiner — Genevieve S Alley

(57) ABSTRACT

A personal care composition is provided that comprises a hydrophilic liquid, a structurant for the hydrophilic liquid, a surface active, a lipid, and an aqueous phase. The lipid, hydrophilic liquid, structurant, and surface active are included in a lipid phase. The hydrophilic liquid, structurant, and surface active are connected to the lipid in the lipid phase. These compositions provide improved skin and/or hair moisturization, appearance, aesthetics and skin and/or hair conditioning during and/or after application, and are useful in providing improved deposition to the desired area of the skin and/or hair. A method of using the personal care composition is also provided.

20 Claims, No Drawings

U.S. PATENT DOCUMENTS

| | | |
|---|---|---|
| 2005/0238680 A1 | 10/2005 | Stella et al. |
| 2005/0239670 A1 | 10/2005 | Stella et al. |
| 2005/0276829 A1 | 12/2005 | Stella et al. |
| 2008/0033058 A1 | 2/2008 | Stella et al. |

FOREIGN PATENT DOCUMENTS

| | | |
|---|---|---|
| EP | 0466236 A1 | 1/1992 |
| EP | 0466237 A1 | 1/1992 |
| EP | 0512270 A2 | 11/1992 |
| EP | 0783881 A2 | 7/1997 |
| EP | 0908172 A1 | 4/1999 |
| EP | 0916662 A2 | 5/1999 |
| EP | 1249232 A1 | 10/2002 |
| FR | 2633515 | 1/1990 |
| GB | 2297762 A | 8/1996 |
| JP | 58180421 | 10/1983 |
| JP | 2200607 | 8/1990 |
| JP | 3223208 | 10/1991 |
| JP | 04243807 | 8/1992 |
| JP | 5032789 A | 2/1993 |
| JP | 05213731 | 8/1993 |
| JP | 6048916 A | 2/1994 |
| JP | 06345633 | 12/1994 |
| JP | 2001-089348 | 4/2001 |
| JP | 2001-288030 | 10/2001 |
| JP | 2003-171230 | 6/2003 |
| JP | 2004-168951 A | 6/2004 |
| KR | 960006857 B | 5/1996 |
| WO | WO-92/19214 A2 | 11/1992 |
| WO | WO-94/24993 A1 | 11/1994 |
| WO | WO 95/00612 A1 | 1/1995 |
| WO | WO 96/31190 A1 | 10/1996 |
| WO | WO-99/26585 A1 | 6/1999 |
| WO | WO-00/47182 A1 | 8/2000 |
| WO | WO-02/096371 A1 | 12/2002 |
| WO | WO-03/059311 A1 | 7/2003 |
| WO | WO-03/074020 A1 | 9/2003 |
| WO | WO-03/094867 A1 | 11/2003 |
| WO | WO-2004/064790 A1 | 8/2004 |
| WO | WO-2004/100921 A1 | 11/2004 |
| WO | WO-2004/103323 A1 | 12/2004 |

\* cited by examiner

PERSONAL CARE COMPOSITIONS THAT DEPOSIT HYDROPHILIC BENEFIT AGENTS

CROSS REFERENCE TO RELATED APPLICATION

This application is a continuation of U.S. patent application Ser. No. 11/103,254 filed Apr. 11, 2005 which claims the benefit of U.S. Provisional Application No. 60/564,259, filed Apr. 21, 2004.

FIELD

The present invention relates to the field of personal care compositions for improving moisturization and appearance and feel of keratinous surfaces. More specifically, the invention relates to rinsable personal care compositions that deposit hydrophilic benefit agents on keratinous surfaces and provide excellent skin and/or hair moisturization, conditioning, tone, and radiance.

BACKGROUND

Personal care compositions are well known and widely used. These compositions have long been employed to cleanse and moisturize skin and/or hair, deliver actives, hide imperfections and to reduce the oiliness/shine associated with sebum. While the compositions and disclosures of the prior art provide useful advances in the art of personal care compositions, additionally, there remains the need for improved personal care compositions that deliver immediate and chronic improvements in skin and/or hair moisturization, appearance and feel, and will effectively deposit on all parts of the body. The compositions also need to be non-greasy and easy to apply.

Some methods of depositing benefit agents commonly used include encapsulation of hydrophilic materials in a hydrophobic shell that is dispersed in hydrophobic lipid carriers for depositing hydrophilic materials on skin and/or hair. However, the deposited hydrophilic materials are not able to be readily released onto skin and/or hair to provide skin and/or hair benefits. The use of water-oil-water emulsions is another way to potentially deposit hydrophilic materials. However, the instability of these types of products often results in a slow leak of hydrophilic materials into the external aqueous phase, and therefore low deposition efficiency. Additional methods of depositing benefit agents include absorbing hydrophilic materials into hydrophilic porous particles for slow release of the hydrophilic material for leave-on application. However, hydrophilic particles by themselves are not effectively deposited onto skin and/or hair from rinse-off applications.

It is desirable to provide an effective level of hydrophilic skin and/or hair benefit materials. However, the deposition of hydrophilic benefit agents such as glycerine, dihydroxyacetone (DHA), and others from a rinse-off application has been a tremendous challenge resulting in no consumer benefit due to low deposition efficiency. Thus, there still remains the need for a rinse-off product that more effectively deposits benefit agents.

SUMMARY

The present invention relates to a personal care composition that comprises a hydrophilic liquid, a structurant for said hydrophilic liquid, a surface active, a lipid, and an aqueous phase, wherein said lipid, said hydrophilic liquid, said structurant, and said surface active form a lipid phase; wherein said lipid, said hydrophilic liquid, said structurant, said surface active are connected to said lipid in a lipid phase. One embodiment of the present invention relates to a personal care composition that comprises a hydrophilic liquid, a structurant for said hydrophilic liquid, a surface active, a lipid, and an aqueous phase, wherein said structurant is selected from the group consisting of fluid absorbent particles, inorganic particulate thickeners, and water soluble or water swellable polymers, and wherein said surface active is selected from the group consisting of association structure forming materials, dialkylquates, ester oils, silicone oils, liquid fatty alcohols and fatty acids, and microfine particles. Another embodiment of the present invention relates to a personal care composition that comprises a hydrophilic liquid, a structurant for said hydrophilic liquid, a surface active, a lipid, and an aqueous phase, wherein said structurant and said surface active are both association structure forming materials. These compositions provide improved skin and/or hair moisturization, appearance, aesthetics and skin and/or hair feel during and/or after application, and are useful in providing improved deposition of actives to the desired area of the skin and/or hair.

DETAILED DESCRIPTION

All percentages and ratios used herein are by weight of the total composition and all measurements made are at 25° C., unless otherwise designated.

The compositions of the present invention can comprise, consist essentially of, or consist of, the essential as well as optional ingredients and components described herein. As used herein, "consisting essentially of" means that the composition or component may include additional ingredients, but only if the additional ingredients do not materially alter the basic and novel characteristics of the claimed compositions or methods. It should be obvious to one skilled in the art that other common personal care materials can be incorporated without altering the substance of the invention.

The term "dermatologically-acceptable", as used herein, means that the compositions or components thereof so described are suitable for use in contact with human skin without undue toxicity, incompatibility, instability, allergic response, and the like.

The term "rinsable composition", as used herein, means a composition designed to be rinsed off by a liquid such as water. After the composition is rinsed off, hydrophilic benefit agents are deposited on the skin and/or hair.

The term "safe and effective amount", as used herein, means an amount of a compound, component, or composition sufficient to significantly induce a positive benefit, preferably a positive skin and/or hair moisturization, appearance or feel benefit, including independently the benefits disclosed herein, but low enough to avoid serious side effects, i.e., to provide a reasonable benefit to risk ratio, within the scope of sound medical judgment.

The term "topical application", as used herein, means to apply or spread the compositions of the present invention onto the surface of the skin.

The term "hydrophilic liquid", as used herein, means that a liquid material has a strong affinity to water.

The term "skin darkening", as used herein, means to impart color to the skin using artificial means, preferably chemical means. This term includes compositions that produce an artificial tan similar to that generated by prolonged exposure to solar radiation, and also those that impart a slight coloration to the skin that are not readily recognized as an artificial tan, but rather generate a subtle color on the skin that makes the skin appear healthier.

The term "structurant for the hydrophilic liquid", as used herein, means a material in combination with a liquid forming a complex with a viscosity higher than the liquid or in a form of solid or semi-solid.

The term "surface active", as used herein, means a material forming a common boundary of a structured hydrophilic liquid and a lipid.

The term "association structure", as used herein, means micelles, reverse micelles, lyotropic liquid crystal structures, and α-crystalline gel structures which are formed by the mixture of a surfactant or the mixture of surfactants and a polar solvent or the mixture of polar solvents at ambient temperature.

The term "liquid crystals" or "liquid crystalline", as used herein, means an intermediate state between the solid and liquid states. It is often called a mesomorphic state. In the literature, liquid crystal structures are also referred to as anisotropic fluids, or in the case of the cubic phase, as isotropic fluids, a fourth state of matter, liquid crystals, aggregates, or mesophases. These terms are used interchangeably. Liquid crystal structures or aggregates are generally disclosed in the reference Lyotropic Liquid Crystals Stig Friberg (Ed.), American Chemical Society, Washington, D.C., 1976, pp 13-27.

The term "α-crystalline gel", as used herein, means a crystalline state of the surfactant with layers of hydrophilic liquid between the polar groups. The structure of the gel is of lamellar type as is the lamellar phase. The difference is that the hydrocarbon chains are in a solid state and orientated parallel to each other in an α-crystalline mode of packing.

The term "connected to", as used herein, means a material or a phase is on the surface, within the domain, or both on the surface and within the domain of another material or a phase.

Active and other ingredients useful herein may be categorized or described herein by their cosmetic and/or therapeutic benefit or their postulated mode of action. However, it is to be understood that the active and other ingredients useful herein can in some instances provide more than one cosmetic and/or therapeutic benefit or operate via more than one mode of action. Therefore, classifications herein are made for the sake of convenience and are not intended to limit an ingredient to the particularly stated application or applications listed.

A. Hydrophilic Liquid

A hydrophilic liquid is a liquid with a strong affinity to water. The hydrophilic liquids include neat liquid materials, mixtures of liquid materials and solid materials dissolved in hydrophilic liquids. The hydrophilic liquids and solids have a solubility of at least 1 g in 100 g of water at 25° C. The personal care compositions preferably comprise no more than about 90 weight percent of the composition of the hydrophilic liquids, more preferably no more than about 70 weight percent, more preferably no more than about 50 weight percent. The personal care compositions preferably comprise at least about 0.1 weight percent of the composition of the hydrophilic liquids, more preferably at least about 0.2 weight percent, even more preferably at least about 0.5 weight percent. The useful skin compatible hydrophilic liquids may include hydrophilic materials including, but not limited to, water, humectants, sugar amines, Vitamin B families, Vitamin C families, Natural extracts, protease inhibitors, α-hydroxyaldehydes and ketones, peptides, water soluble or swellable polymers, and mixtures thereof. The skin benefits provided by these materials include moisturization, softness, feel, shine, desquamation, barrier improvement, wrinkle repair, anti-yellowing/sallowness, anti-irritancy, soothing, darkening, lightening, hair growth reduction, hair styling and hair conditioning.

Suitable skin compatible solvents to dissolve solid hydrophilic materials include, but are not limited to water, alcohols (e.g. ethanol, glycerin), polyols (e.g. Polyethyleneglycol), hydrophilic oils and/or their mixtures.

1. Humectants

The compositions of the present invention may contain a humectant. The humectants herein are selected from the group consisting of water, polyhydric alcohols, amino acids, pyrrolidone carboxylic acid and salt, hydroxyl acids, urea, urea derivatives and water soluble alkoxylated nonionic polymers, and mixtures thereof.

Polyhydric alcohols useful herein include glycerin, sorbitol, propylene glycol, butylene glycol, hexylene glycol, ethoxylated glucose, 1,2-hexane diol, hexanetriol, dipropylene glycol, erythritol, trehalose, diglycerin, xylitol, maltitol, maltose, glucose, fructose, sodium chondroitin sulfate, sodium hyaluronate, sodium adenosine phosphate, sodium lactate, pyrrolidone carbonate, glucosamine, cyclodextrin, and mixtures thereof.

Hydroxyl acids useful herein include lactic acid and glycolic acid, salicylic acid and their salts, and mixtures thereof.

Water soluble alkoxylated nonionic polymers useful herein include polyethylene glycols and polypropylene glycols having a molecular weight of up to about 1000 such as those with CTFA names PEG-200, PEG-400, PEG-600, PEG-1000, and mixtures thereof.

2. Electrolytes

The compositions of the present invention may include a safe and effective amount of an electrolyte. Non-limiting examples include sodium salts, potassium salts, calcium salts, and mixtures thereof.

3. Sugar Amines

The compositions of the present invention may include a safe and effective amount of a sugar amine, which are also known as amino sugars. As used herein, "sugar amine" refers to an amine derivative of a six-carbon sugar. Examples of sugar amines that are useful herein include glucosamine, N-acetyl glucosamine, mannosamine, N-acetyl mannosamine, galactosamine, and N-acetyl galactosamine.

4. Vitamin B Family

The compositions of the present invention may contain a safe and effective amount of a compound from the Vitamin B Family. In one embodiment, the compositions of the present invention can contain a vitamin $B_3$ compound. Vitamin $B_3$ compounds are particularly useful for regulating skin condition as described in U.S. Pat. No. 5,939,082. As used herein, "vitamin $B_3$ compound" means a compound having the formula:

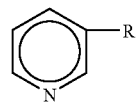

wherein R is —$CONH_2$ (i.e., niacinamide), —COOH (i.e., nicotinic acid) or —$CH_2OH$ (i.e., nicotinyl alcohol); salts, derivatives, and mixtures thereof.

The compositions of the present invention may include a safe and effective amount of a panthenoic acid derivative, including panthenol, dexpanthenol, ethyl panthenol, and mixtures thereof. These vitamin $B_5$ compounds provide skin soothing, moisturizing, and anti-irritating benefits.

The topical compositions of the present invention may comprise a safe and effective amount of one or more vitamin $B_6$ compounds selected from the group consisting of pyridoxine, esters of pyridoxine (e.g., pyridoxine tripalmitate), amines of pyridoxine (e.g., pyridoxamine), salts of pyridoxine (e.g., pyridoxine HCl) and derivatives thereof, including pyridoxamine, pyridoxal, pyridoxal phosphate, pyridoxic acid, and mixtures thereof. Vitamin $B_6$ can be synthetic or natural in origin and can be used as pure compounds or mixtures of compounds (e.g., extracts from natural sources or mixtures of synthetic materials). Vitamin $B_6$ is generally found in many foodstuffs, especially yeast, liver and cereals. As used herein, "vitamin $B_6$" includes isomers and tautomers of such. Vitamin $B_6$ is commercially available from Sigma Chemical Co.

5. Vitamin C Family

The compositions of the present invention may include a safe and effective amount of a compound from the Vitamin C Family. Specifically, the compositions may include ascorbic acid and its salts, and ascorbic acid derivatives (e.g. magnesium ascorbyl phosphate, sodium ascorbyl phosphate, ascorbyl sorbate, ascorbyl glucoside, and mixtures thereof). These anti-oxidant/radical scavengers are especially useful for providing protection against UV radiation which can cause increased scaling or texture changes in the stratum corneum and against other environmental agents which can cause skin damage.

6. Natural Extracts

The compositions of the present invention may include a safe and effective amount of extracts from natural products. Non-limiting examples include mulberry extract, placental extract, soy extract, green tea extract, and chamomile extract. These extracts provide a broad range of skin benefits such as anti-inflammatory, skin lightening, hair growth reduction and anti-irritancy.

7. Peptides

The compositions of the present invention may contain a safe and effective amount of a peptide, including but not limited to, di-, tri-, tetra-, penta-, hexa-peptides, and derivatives and mixtures thereof. As used herein, "peptide" refers to peptides containing ten or fewer amino acids and their derivatives, isomers, and complexes with other species such as metal ions (e.g., copper, zinc, manganese, magnesium, and the like). As used herein, peptide refers to both naturally occurring and synthesized peptides. Also useful herein are naturally occurring and commercially available compositions that contain peptides.

8. Alpha-Hydroxy Aldehydes and Ketones

The compositions of the present invention may include alpha-hydroxy aldehydes and ketones. Examples include, but are not limited to, dihydroxyacetone, glyceraldehydes, 2,3-dihydroxy-succindialdehyde, 2,3-dimethoxysuccindialdehyde, erythrulose, erythrose, 2-amino-3-hydroxy-succindialdehyde and 3-benzylamino-3-hydroxy-succindialdehye. These compounds have a sun-less tanning benefit when applied to skin. As used herein, the term "sun-less tanning" is defined as color darkening to the skin using artificial means, preferably chemical means. This term includes compositions that produce an artificial tan similar to that generated by prolonged exposure to solar radiation, and also those that impart a slight coloration to the skin that are not readily recognized as an artificial tan, but rather generate a subtle color on the skin that makes the skin appear healthier.

9. Hexamidine

The topical compositions of the present invention may comprise a safe and effective amount of one or more hexamidines and their salts. Preferably, the hexamidine is hexamidine isethionate. As used herein, "hexamidine" includes any isomers and tautomers of such. Hexamidine is commercially available as hexamidine isethionate under the tradename Elastab® HP100 from Laboratoires Serobiologiques.

10. Dehydroacetic Acid

The compositions of this invention may comprise dehydroacetic acid or its salts, derivatives, or tautomers thereof. These compounds are useful in (i) reducing sebum synthesis by the pilosebaceous glands, (ii) regulating the oily and/or shiny appearance of the skin, and (iii) treating acne and other related skin disorders in mammalian skin and scalp.

Dermatologically acceptable salts include alkali metal salts, such as sodium and potassium; alkaline earth metal salts, such as calcium and magnesium; non-toxic heavy metal salts; ammonium salts; and trialkylammonium salts, such as trimethylammonium and triethylammonium, and mixtures thereof. Sodium, potassium, and ammonium salts of dehydroacetic acid are preferred. Derivatives of dehydroacetic acid include, but are not limited to, any compounds wherein the $CH_3$ groups are individually or in combination replaced by amides, esters, amino groups, alkyls, and alcohol esters. Tautomers of dehydroacetic acid are the isomers of dehydroacetic acid which can change into one another with great ease so that they ordinarily exist in equilibrium. Thus, tautomers of dehydroacetic acid can be described as having the chemical formula $C_8H_8O_4$.

11. Water-Soluble or Water-Swellable Polymer

The polymers useful in this invention are any water-soluble or water-swellable polymer suitable for use in personal care products and for application to human skin and hair. The polymers may be homopolymers, copolymers or a blend of polymers or copolymers. The polymers can be natural, synthetic, or semi-synthetic. Polymers can be straight chain or cross-linked. Polymers, containing either ionic and non-ionic groups, are contemplated. Ionic polymers include, but are not limited to, cationic, anionic, zwitterionic, and amphoteric polymers. The polymers can be synthesized from a variety of monomers containing unsaturated groups or by synthetic mechanisms that result in a variety of linking groups, including polyurethanes, polyesters, polyamides, and polyureas in the polymer backbone.

Examples of useful commercially available synthetic polymers are listed below. The names described are according to the nomenclature developed by the Cosmetic, Toiletry, and Fragrance Association, Inc. (CTFA). In few cases, where the CTFA name is not available, the chemical name is written. Non-limiting examples include: vinylcaprolactam/PVP/dimethylamino-ethylmethacrylate copolymer (trade name: Gaffic, H2OLD, ISP Corp.), vinyl acetate/crotonic acid/vinyl propionate copolymer (trade name: Luviset, BASF), vinyl acetate/crotonates copolymer (trade name: Resyn, National Starch Corp.), vinyl acetate/butyl maleate/isobornyl acrylate copolymer (trade name: Advantage CPV, ISP), tyrene/vinylpyrrolidone copolymer (trade name: Polectron, ISP); vinylpyrrolidone/vinyl acetate copolymers (ISP, BASF); polyvinylpyrrolidone/polyurethane interpolymer (Pecogel, Phoenix); octylacrylamide/acrylates/butylaminoethylmethacrylate copolymer (Amphomer, National Starch); quaternized vinylpyrrolidone/dimethylaminoethyl methacrylate copolymer (Polyquaternium-11, ISP), vinylpyrrolidone/vinyl acetate/vinyl propionate copolymer (Luviskol, BASF). In addition, other commercially available polymers listed in the Encyclopedia of Polymers and Thickeners, Cosmetic and Toiletries, page 95, Vol. 108, May 1993 can be included in this invention.

Examples of natural and modified natural polymers are: copolymer of hydroxyethyl-cellulose and dimethyldiallyl ammonium chloride (Polyquaternium-4; National Starch), hydroxyethyl-cellulose (Natrosol; Aqualon), xanthan gum (Calgon), and other polymers listed in the Encyclopedia of Polymers and Thickeners, Cosmetic and Toiletries, page 95, Vol. 108, May 1993 can be included in this invention.

Polymers that may be useful in the present invention are silicone graft copolymers listed in the U.S. Pat. Nos. 5,565,193 and 5,622,694; hydrophobic graft copolymers are listed in U.S. Pat. No. 5,622,694; silicone block copolymers are listed in U.S. Pat. No. 6,074,628.

The water-soluble or water-swellable polymers of the present invention may also include carboxylic acid/carboxylate copolymers. The carboxylic acid/carboxylate copolymers herein can include cross-linked copolymers of carboxylic acid and alkyl carboxylate, and can have an amphophilic property. Commercially available carboxylic acid/carboxylate copolymers useful herein include: CTFA name Acrylates/$C_{10-30}$ Alkyl Acrylate Crosspolymer having tradenames Pemulene TR-1, Pemulene TR-2, Carbopol 1342, Carbopol 1382, and Carbopol ETD 2020, all available from B. F. Goodrich Company.

12. Colorants

The composition of the present invention may include a colorant. In general, colorants are those substances that provide color to a personal care product. The purpose of the colorant is to deliver the desirable shade or color to skin or hair that the user is seeking as well as to even out skin tone by covering or hiding tonal imperfections. Such colorants should be physically and chemically compatible with the essential components described herein, or should not otherwise unduly impair product stability, aesthetics or performance. Useful colorants herein include water soluble dyes. Water soluble dyes, identified by one skilled in the art, are dyes that are substantially soluble in aqueous solutions. Non-limiting examples of water soluble acid dyes include D&C Red 33, FD&C Yellow No. 5, D&C Green No. 5, D&C Yellow No. 8, and D&C Yellow No. 10.

The composition of the present invention may include an oxidizing agent (e.g. peroxides), and/or oxidative dye precursors (including developers and/or couplers when present).

B. Structurant for the Hydrophilic Liquid

The compositions of the present invention may contain a structurant for the hydrophilic liquid. A structurant mixed with a liquid forms a complex with a viscosity higher than the liquid or in a form of solid or semi-solid. The combination of the hydrophilic liquid and structurant form a material having a preferred viscosity of at least about 3000 cst (centistokes) at 25° C., preferably at least about 5000 cst. The structurants herein are used to immobilize hydrophilic liquids. Useful structurants include association structure forming materials, fluid absorbent particles, inorganic particulate thickeners, and water-soluble or water-swellable polymers. Preferably the ratio of structurant to hydrophilic liquid is from about 1:1000 to about 100:1, more preferably from about 1:200 to about 80:1, still more preferably from about 1:100 to about 50:1, and even more preferably from about 1:20 to about 20:1.

1. Association Structure Forming Materials

The personal care compositions of the present invention may include association structure forming materials. The association structure forming materials comprise from about 0.1% to about 80% of the personal care composition. Preferably the association structure forming materials comprise from about 0.2% to about 70%, of the personal care composition.

Use of the association structure forming materials in the present invention provides a method of encapsulating active ingredients. The active ingredients are encapsulated by combining a surface active (described herein) and a hydrophilic liquid (described herein) to form an association structure; dispersing the association structure in a lipid phase (described herein); and dispersing the lipid phase in an aqueous phase (described herein).

The association structures of the present invention may be micelles, reverse micelles, lyotropic liquid crystals, α-crystalline gels and mixtures thereof. Reverse micelles are also known in the art as spherical reverse micelles, elongated reverse micelles, bicontinuous phase or L2 phase; cylindrical reverse micelles or reverse connected rod-shaped liquid crystals also known in the art as networking reverse cylinders, connected cylindrical reverse micelle structures, or connected cylinders. Lyotropic Liquid Crystals include: 1) reverse hexagonal liquid crystals, also known in the art as hexognal II or F phase; 2) cubic liquid crystals, also known in the art as viscous isotropic and $I_2$ phase; 3) lamellar liquid crystals, also known in the art as the Lα neat phase and D phase; and 4) cholesteric liquid crystals, an anisotropic subclass of polymeric lyotropic liquid crystal. The centers of gravity of the polymeric particles are arranged at random with no positional order, but only an orientational order exists. Preferred association structures are the cylindrical reverse micelle, reverse hexagonal liquid crystals, cubic liquid crystals, lamellar liquid crystals, cholesteric liquid crystals, and mixtures thereof. The association structures can be in the following phases: two phase liquid crystals, one phase liquid crystals, reverse micelles/liquid crystalline phase or liquid crystalline/solvent phase.

Any surfactant and/or polymers which forms association structures at ambient temperature and is suitable for use in personal care compositions, is suitable for use herein. Surfactants suitable for use in personal care compositions do not present dermatological or toxicological problems. Anionic surfactants, nonionic surfactants, cationic surfactants, amphoteric surfactants and mixtures thereof are suitable for use. Types of anionic surfactants suitable for use are soaps; sulfonates such as alkane sulfonates (e.g., branched sodium x-alkane sulfonate where x≠1) paraffin sulfonates, alkylbenzene sulfonates, a-olefin sulfonates, sulfosuccinates and sulfosuccinate esters (e.g., dioctylsodium and disodium laureth sulfosuccinate), oisethionates, acylisethionates (e.g., sodium 2-lauroyloxyethane sulfonate), and sulfalkylamides of fatty acids, particularly N-acylmethyltaurides; sulfates such as alkyl sulfates, ethoxylated alkyl sulfates, sulfated monoglycerides, sulfated monoglycerides, sulfated alkanolamides, and sulfated oils and fats; carboxylates such as alkyl carboxylate having a carbon chain length above $C_{12}$, acylsarcosinates, sarcosinates (e.g., sodium lauryl sarcosinate), ethoxylated carboxylic acid sodium salts, carboxylic acids and salts (e.g., potassium oleate and potassium laurate), ether carboxylic acids; ethoxylated carboxylic acids and salts (e.g., sodium carboxymethyl alkyl ethoxylate; phosphoric acid esters and salts (e.g., lecithin); acylglutamates (e.g., disodium n-lauroyl glutamate) and mixtures thereof. It should be noted that the safest alkyl sulfates for use generally have a hydrocarbon chain lengths above $C_{12}$.

Types of nonionic surfactants suitable for use are polyoxyethylenes such as ethoxylated fatty alcohols, ethoxylated alcohols (e.g., octaoxyethelene glycol mono hexadecyl ether, $C_{16}E_8$ and $C_{12}E_8$), ethoxylated fatty acids, ethoxylated fatty amines, ethoxylated fatty amides, ethoxylated alkanolamides, ethoxylated alkyl phenol, and ethoxylated sterols; triesters of phosphoric acid (e.g., sodium dioleylphosphate); alkyl amido diethylamines; alkylamido propylbetaines (e.g., cocoamido propylbetaine); amine oxide derivatives such alkyl dimethylamine oxides, alkyl dihydroxyethylamine oxides, alkyl amidodimethylamine oxides and alkyl amidodihydroxyethylamine oxides; polyhydroxy derivatives such as polyhydric alcohol esters and ethers (e.g., sucrose monooleate, cetostearyl glucoside, β octyl glucofuranoside, esters, alkyl glucosides having a carbon chain length of from $C_{10}$ to $C_{16}$), mono, di- and polyglycerol ethers and polyglycerol esters (e.g., tetraglycerol monolaurate and monoglycerides, triglycerol monooleate (such as TS-T122 supplied by Grinsted), diglycerol monooleate (such as TST-T101 supplied by Grinsted), ethoxylated glycerides; monoglycerides such as monoolein, monolaurin and monlinolein; diglyceride fatty acids such as diglycerol monoisostearate (e.g., Cosmol 41 fractionated supplied by Nisshin oil Mills, Ltd.) and mixtures thereof.

Types of cationic surfactants suitable for use are aliphatic-aromatic quaternary ammonium halides; quaternary ammonium alkyl amido derivatives; alkyl amidopropyldimethylammonium lactate; alkylamidopropyldihydroxyethylammo-nium lactate; alkyl amidopropyl morpholinium lactate; quaternary ammonium lanolin salts; alkyl pyridinium halides; alkyl isoquinolinium halides; alkyl isoquinolinium halides; quaternary ammonium imidazolinium halides; bisquaternary ammonium derivatives; alkylbenzyl dimethylammonium salts such as stearalkylammonium chloride; alkylbetaines such as dodecyldimethylammonium acetate and oleylbetaine; alkylethylmorpholinium ethosulfaates; tetra alkyl ammonium salts such as dimethyl distearyl quaternary ammonium chloride and bis isostearamideopropyl hydroxypropyl diammonium chloride (Schercoquat 2IAP from Scher Chemicals); heterocyclic ammonium salts; bis(triacetylammoniumacetyl) diamines and mixtures thereof.

Types of amphoteric surfactants suitable for use are alkyl betaines; alkanolamides such as monoalkanolamides and dialkanolamides; alkyl amido propylbetaines; alkyl amidopropylhydroxysultaines; acylmonocarboxy hydroxyethyl glycinates; acyldicarboxy hydroxyethyl glycinates; alkylaminopropionates such as sodium laurimino dipropionate; alkyl iminodipropionates; amine oxides; acyl ethylenediamine betaines; N-alkylamino acids such as sodium N-alkylamino acetate; N-lauroylglutamic acid cholesterol esters; alkyl imidazolines and mixtures thereof. Association structure forming materials may include polymers such as alkoxylated polymers and polysaccharides. The polymers may have a molecular weight of from about 500 to about 1,000,000. Lower molecular weight polymers within the range of from about 750 to about 500,000 are preferred, and those with molecular weights of from about 1,000 to about 60,000 are even more preferred. Polysaccharides useful in the present invention include polyglucose materials, gums, hydrocolloids, cellulose and cellulose-derivative polymers. Many of these and other suitable polysaccharides are described in *Industrial Gums—Polysaccharides and Their Derivatives*, Roy L. Whistler, Academic Press (New York), 1959 and also in P. Weigel et al., "Liquid Crystalline States in Solutions of Cellulose and Cellulose Derivatives," Acta Polymerica Vol. 35 No. 1, 1984, pp. 83-88. Useful polysaccharides include nonionic, anionic and cationic polysaccharides. Preferred nonionics include the hydroxypropyl cellulose polymers known as the KLUCEL series available from Hercules, Inc. and xantham guy available from Kelco. Preferred anionic polymers are the sodium alginates (available from Kelco) and sodium carboxymethylcellulose polymer available from Hercules. Preferred cationic polymers are CHITOSAN and CHITIN from Protan, Inc, and also depolymerised guar, such as T4406 from Hi Tek Polymers. Alkoxylated polymers useful in the present invention include the Poloxamer Series of EO-PO condensates (A-B-A type block copolymers of polyoxyethylene and polyoxypropylene). Suitable examples of polyoxyethylene-polyoxypropylene block copolymers include Poloxamers 403, 402, and 401 available under the tradenames PLURONIC P123, PLURONIC L-122, and PLURONIC L-121 from BASF and Hodag Nonionic 1123-P and Hodan Nonionc 1122-L from Calgene and SYNPERONIC PE/L121 from ICI.

Also useful herein are silicone copolyols and aminosilicones. Suitable examples include DC-190, DC-193, DC5329, Q4-3667 from Dow Corning; Silwet L-7622 and Silwet L-77 from Union Carbide.

2. Fluid Absorbent Particles

The compositions of the present invention may comprise fluid-absorbent particles. The fluid-absorbent particles can be any material that remains solid within the composition, including porous, hydrophilic, and solid particles. The fluid absorbent particles may have an average particle size of from about 0.001 microns to about 2000 microns, preferably from about 0.01 microns to about 200 microns, more preferably from about 0.1 microns to about 100 microns. The fluid-absorbent particles for use in the compositions of the present invention include moisture-absorbent materials such as silicas (or silicon dioxides), silicates, carbonates, various organic copolymers, and combinations thereof. The silicates are most typically those formed by reaction of a carbonate or silcate with an alkali metal, alkaline earth metal, or transition metal, specific non-limiting examples of which include calcium silicate, amorphous silicas (e.g., precipitated, fumed, and colloidal), calcium carbonate (e.g., chalk), magnesium carbonate, zinc carbonate, and combinations thereof. Non-limiting examples of some suitable silicates and carbonates for use herein are described in Van Nostrand Reinhold's *Encyclopedia of Chemistry*, $4^{th}$ edition, pages 155, 169, 556, and 849 (1984). Absorbent powders are also described in U.S. Pat. No. 6,004,584.

Other fluid-absorbent particles suitable for use herein include kaolin, (hydrated aluminum silicates), mica, talc (hydrated magnesium silicates), starch or modified starch, microcrystalline cellulose (e.g., Avicel from FMC Corporation), or other functionally similar fluid-absorbent polymer, any other silica-containing or non-silica-containing powder.

Other fluid-absorbent particles suitable for the use herein include super-absorbent polymers. By definition, a superabsorbent polymer must absorb a minimum of 20 times its own weight in water. Moreover, the polymer must retain its original identity and have sufficient physical integrity to resist flow and fusion with neighboring particles, and to swell to equilibrium volume and not dissolve. Non-limiting examples include Water Lock® superabsorbent polymers (e.g. Starch graft poly(2-propenamide-co-2-propenoic acid) sodium or potassium salt, 2-propenamide-co-2-propenoic acid copolymer, sodium salt) manufactured by Grain Processing Corporation.

3. Inorganic Particulate Thickeners

The compositions of the invention may also include inorganic particulate thickener. These inorganic particles form a stable network with hydrophilic liquids. Non-limiting examples include silica and clay (e.g. Benton clays from Rhox) with particle size less than 1 micrometer.

4. Water-Soluble or Water-Swellable Polymers

Description is same as above in the hydrophilic liquid section.

C. Surface Active

The compositions of the present invention include surface actives. The surface actives form a common boundary of a structured hydrophilic liquid and a lipid. The surface actives contain polar groups and non-polar groups. This property can be measured by a contact angle method. The contact angles of the surface actives on both a hydrophobic surface (polyethylene terephthalate) and a hydrophilic surface (aluminum foil) are no more than 60°, preferably no more than 50°, and even more preferably no more than 40° for materials which can be applied to the surfaces as drops. Contact angles of diiodomethane and water on thin films of surface actives that are too thick to form drops on the solvent surfaces are no more than 90°, preferably no more than 80°, even more preferably no more than 70°. Preferably the solubility parameter of surface actives is at least 3 units different from that of the hydrophilic liquid, more preferably at least 4 units different, still more preferably at least 5 units from that of the hydrophilic liquid. Preferably the solubility parameter of the surface actives is at least 1 unit different from that of the lipid described herein, more preferably at least 1.5 units different and even more preferably at least 2 units different from that of the lipid. The ratio of surface active to hydrophilic liquid is from about 1:1000 to about 20:1, more preferably from about 1:100 to about 15:1, still more preferably from about 1:10 to about 10:1.

The surface actives can be combined with the structured hydrophilic liquids during formulating the product. Alternatively, the structured hydrophilic liquids can be treated with the surface actives by a surface treatment house (e.g. KOBO products, US Cosmetics).

1. Association Structure Forming Materials

In one embodiment of the present invention, both the structurant for the hydrophilic liquid and the surface active are association structure forming materials. The description is the same as above in the structurant for the hydrophilic liquid section.

2. Film Forming Materials

In one embodiment of the present invention, the structurant for the hydrophilic liquid and the surface active are not both association structure forming materials. In this embodiment, the surface active may be film forming materials selected from dialkylquates, ester oils, silicone oils and waxes, liquid fatty alcohols and fatty acids, and microfine particles.

a. Dialkylquates

The present compositions may include a dialkylquaternary compound. Non-limiting examples include dialkyl dimethyl quaternaries (e.g. dialkyl($C_{12}$-$C_{18}$)dimethyl ammonium chloride, ditallow dimethyl ammonium chloride, distearyl dimethyl ammonium methyl sulfate) and imidazolinium quaternaries (e.g. methyl-1-oleyl amido ethyl-2-oleyl imidazolinium-methyl sulfate).

b. Ester Oils

Ester oils have at least one ester group in the molecule. One type of common ester oil useful in the present invention are the fatty acid mono and polyesters such as cetyl octanoate, octyl isonanoanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate; sucrose ester and polyesters, sorbitol ester, and the like. A second type of useful ester oil is predominantly comprised of triglycerides and modified triglycerides. These include vegetable oils such as jojoba, soybean, canola, sunflower, safflower, rice bran, avocado, almond, olive, sesame, persic, castor, coconut, and mink oils. Synthetic triglycerides can also be employed provided they are liquid at room temperature. Modified triglycerides include materials such as ethoxylated and maleated triglyceride derivatives provided they are liquids. Proprietary ester blends such as those sold by Finetex as Finsolv are also suitable, as is ethylhexanoic acid glyceride. A third type of ester oil is liquid polyester formed from the reaction of a dicarboxylic acid and a diol. Examples of polyesters suitable for the present invention are the polyesters marketed by ExxonMobil under the trade name PURESYN ESTER®.

c. Silicone Oils and Waxes

The compositions of the present invention may include silicone oils and waxes. Silicone oils and waxes include polydimethyl siloxane, organo functional silicones (alkyl and alkyl aryl, copolyol), and amino silicones.

d. Liquid Fatty Alcohols and Fatty Acids

The liquid fatty alcohols useful herein include those having from about 10 to about 30 carbon atoms. These liquid fatty alcohols may be straight or branched chain alcohols and may be saturated or unsaturated alcohols. Liquid fatty alcohols are those fatty alcohols which are liquid at 25° C. Nonlimiting examples of these compounds include oleyl alcohol, palmitoleic alcohol, isostearyl alcohol, isocetyl alcohol, and mixtures thereof. While poly fatty alcohols are useful herein, mono fatty alcohols are preferred.

The fatty acids useful herein include those having from about 10 to about 30 carbon atoms. These fatty acids can be straight or branched chain acids and can be saturated or unsaturated. Suitable fatty acids include, for example, oleic acid, linoleic acid, isostearic acid, linolenic acid, ethyl linolenic acid, arachidonic acid, ricinolic acid, and mixtures thereof.

e. Microfine Particles

The present compositions may include microfine particles as surface actives. The microfine particles are dispersible both in water and in oil. The average diameter of the particles used is from about 1 nm to about 200 nm. Advantageous particles are all those which are suitable for stabilizing water-in-oil Pickering emulsions. The amphiphilic characteristics can also be achieved with the surface treatments of these microfine particles. Non-limiting examples of microfine particles include metal oxides and boron nitrides. Non-limiting surface coatings include silicones, silicone derivatives, silica gel, aluminium hydroxide, and alumina.

D. Lipid/Lipid Phase

The composition of the present invention may include a skin compatible lipid. A skin compatible lipid is defined herein, as a lipid that is liquid, semi-solid, or solid at the temperature at which bathing is carried out that is deemed safe for use in cosmetics being either inert to the skin or actually beneficial. Lipids useful herein may include oils and waxes. Useful skin compatible lipids for the present invention include ester lipids, hydrocarbon lipids, and silicone lipids.

Ester lipids have at least one ester group in the molecule. One type of common ester lipids useful in the present invention are the fatty acid mono and polyesters such as cetyl octanoate, octyl isonanoanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate, sucrose ester and polyesters, sorbitol ester, and the like.

A second type of useful ester lipids is predominantly comprised of triglycerides and modified triglycerides. These include vegetable oils such as jojoba, soybean, canola, sunflower, safflower, rice bran, avocado, almond, olive, sesame, persic, castor, coconut, and mink oils. Synthetic triglycerides can also be employed provided they are liquid at room temperature. Modified triglycerides include materials such as ethoxylated and maleated triglyceride derivatives provided they are liquids. Proprietary ester blends such as those sold by Finetex as Finsolv are also suitable, as is ethylhexanoic acid glyceride.

A third type of ester lipids is liquid polyester formed from the reaction of a dicarboxylic acid and a diol. Examples of polyesters suitable for the present invention are the polyesters marketed by ExxonMobil under the trade name PURESYN ESTER®.

A second class of skin compatible lipids suitable for the present invention is liquid and semi-solid hydrocarbons. These include linear and branched oils such as liquid paraffin, squalene, squalane, mineral oil, low viscosity synthetic hydrocarbons such as polyalphaolefin sold by ExxonMobil under the trade name of PURESYN PAO and polybutene under the trade name PANALANE or INDOPOL. Light (low viscosity), highly branched hydrocarbon oils are also suitable.

Petrolatum is a hydrocarbon material and a useful component of the present invention. Its semi-solid nature can be controlled both in production and by the formulator through blending with other oils.

A third class of useful skin compatible lipids is silicone based. They include linear and cyclic polydimethyl siloxane, organo functional silicones (alkyl and alkyl aryl), and amino silicones.

A fourth class of useful skin compatible lipids is liquid fatty alcohols. Useful liquid fatty alcohols herein include those having from about 10 to about 30 carbon atoms. These liquid fatty alcohols may be straight or branched chain alcohols and may be saturated or unsaturated alcohols. Liquid fatty alcohols are those fatty alcohols which are liquid at 25° C. Nonlimiting examples of these compounds include oleyl alcohol, palmitoleic alcohol, isostearyl alcohol, isocetyl alcohol, and mixtures thereof. While poly fatty alcohols are useful herein, mono fatty alcohols are preferred.

A fifth class of useful skin compatible lipids is liquid fatty acids. The liquid fatty acids useful herein include those having from about 10 to about 30 carbon atoms. These fatty acids can be straight or branched chain acids and can be saturated or unsaturated. Suitable fatty acids include, for example, oleic acid, linoleic acid, isostearic acid, linolenic acid, ethyl linolenic acid, arachidonic acid, ricinolic acid, and mixtures thereof.

The lipids of the present invention may be part of a lipid phase. The lipid phase is comprised of three components: a skin compatible lipid, a complex containing a hydrophilic liquid and a structurant, and a surface active. The complex containing a hydrophilic liquid and a structurant is wrapped with the surface active and mixed with the lipid, forming a lipid phase. The hydrophilic liquid, the structurant, and the surface active may be on the surface of the lipid, within the domain of the lipid, or both on the surface and within the domain of the lipid in the lipid phase. The lipid phase is then mixed with the aqueous phase. The lipid phase may be either dispersed in the aqueous phase, connected to the aqueous phase, or both dispersed and connected to the aqueous phase.

To ensure effective deposition and retention to the skin, the lipid phase or structured lipid phase should have a viscosity in the range of from about 100 to about 200,000 poise measured at 1 Sec$^{-1}$, preferably from about 200 to about 100,000 poise, and even more preferably from about 200 to about 50,000 poise as determined using the Lipid Rheology Method described herein.

As the lipid phase may be connected to the aqueous phase, the lipid phase will have negligible solubility in the aqueous phase. The shear index is a measure of how shear thinning the materials are as described in the Lipid Rheology Method described herein. It is preferred that the skin compatible lipid be shear thinning either by virtue of its composition or the structurants that may be added. Preferably, the shear index of the dispersed lipid phase will be less than about 0.9, more preferably less than about 0.75, even more preferably less than about 0.6, even more preferably less than about 0.45, and still more preferably less than about 0.3.

The lipid phase preferably comprises no more than about 95 weight percent of the lipid, preferably no more than about 90 weight percent, and more preferably no more than about 85 weight percent of the lipid. The lipid phase preferably comprises at least about 1 weight percent, more preferably at least about 5 weight percent, and still more preferably at least about 10 weight percent of the lipid.

The composition preferably comprises no more than about 95 weight percent of the lipid phase, preferably no more than about 90 weight percent, and more preferably no more than about 85 weight percent of the lipid phase. The composition preferably comprises at least about 1 weight percent, more preferably at least about 5 weight percent, and still more preferably at least about 10 weight percent of the lipid phase.

The lipid phase may also contain oil-soluble or dispersible skin benefit materials. Non-limiting examples include oil-soluble sun screens, particles (e.g. silica, talc), surface modified particles, pigments (e.g. metal oxides, interference pigment, metallic pigment), oil-soluble dyes, and perfumes.

E. Aqueous Phase

The compositions of the present invention may include an aqueous phase. The aqueous phase of the present invention preferably comprises no more than about 90 weight percent of a fluid, more preferably no more than about 85%, even more preferably no more than about 80%. The aqueous phase of the present invention preferably comprises at least about 10 weight percent of a fluid, more preferably at least about 15%, even more preferably at least about 20%. The term "fluid" as used herein means water, mono- and polyhydric alcohols (glycerin, propylene glycol, ethanol, isopropanol, etc.), or any liquid material which is water miscible. The lipid phase described above may be on the surface and/or within the domain of said aqueous phase. Also, the lipid phase may be one visually distinct phase that is packaged in physical contact with the aqueous phase while maintaining stability.

In one embodiment, there composition may not comprise an aqueous phase. In absence of the aqueous phase, the product forms include, but are not limited to, lipid based liquids and/or solid bars.

The compositions of the present invention may include one or more structurants in the aqueous phase. The structurant may act as a thickener to increase the viscosity of the aqueous phase. The structurant may also form vesicles or other structures to form domains of water in the aqueous phase. The advantage of using an aqueous phase structurant is to further decrease the mobility of water, and as a result, lower the tendency of hydrophilic actives to quickly partition into the aqueous phase. Because different structurants may interact with the aqueous phase with different efficiencies, it is difficult to provide an accurate compositional range. However, when present, the composition preferably comprises no more than about 20 weight percent, more preferably no more than about 15 weight percent, and still more preferably no more than about 10 weight percent of the personal care composition. When present, the aqueous phase structurant preferably comprises at least about 0.01 weight percent, more preferably at least about 0.05 weight percent, and still more preferably at least about 0.1 weight percent of the personal care composition.

Non-limiting examples of inorganic water structurants for use in the personal care composition include silicas, clays such as a synthetic silicates (Laponite XLG and Laponite XLS from Southern Clay), or mixtures thereof.

Non-limiting examples of charged polymeric water structurants for use in the personal care composition include Acrylates/Vinyl Isodecanoate Crosspolymer (Stabylen 30 from 3V), Acrylates/C10-30 Alkyl Acrylate Crosspolymer (Pemulen TR1 and TR2), Carbomers, Ammonium Acryloyldimethyltaurate/VP Copolymer (Aristoflex AVC from Clariant), Ammonium Acryloyldimethyltaurate/Beheneth-25 Methacrylate Crosspolymer (Aristoflex HMB from Clariant), Acrylates/Ceteth-20 Itaconate Copolymer (Structure 3001 from National Starch), Polyacrylamide (Sepigel 305 from SEPPIC), or mixtures thereof.

Non-limiting examples of water soluble polymeric structurants for use in the personal care composition include cellulosic gel, hydroxypropyl starch phosphate (Structured XL from National Starch), polyvinyl alcohol, or mixtures thereof.

Nonlimiting examples of associative water structurants for use in the personal care composition include xanthum gum, gellum gum, pectin, alginate, or mixtures thereof.

Nonlimiting examples of associative water structurants for use in the personal care composition include phospholipids (e.g. lecithin), dialkylquats and other association structure forming materials described above in the structurant for the hydrophilic liquid section.

F. Optional Ingredients

The compositions of the present invention may contain one or more additional skin care components in either the aqueous phase or the lipid phase. In a preferred embodiment, where the composition is to be in contact with human keratinous tissue, the additional components should be suitable for application to keratinous tissue, that is, when incorporated into the composition they are suitable for use in contact with human keratinous tissue without undue toxicity, incompatibility, instability, allergic response, and the like within the scope of sound medical judgment.

The *CTFA Cosmetic Ingredient Handbook*, Second Edition (1992) describes a wide variety of nonlimiting cosmetic and pharmaceutical ingredients commonly used in the personal care industry, which are suitable for use in the compositions of the present invention.

In any embodiment of the present invention, however, the additional components useful herein can be categorized by the benefit they provide or by their postulated mode of action. However, it is to be understood that the additional components useful herein can in some instances provide more than one benefit or operate via more than one mode of action. Therefore, classifications herein are made for the sake of convenience and are not intended to limit the active to that particular application or applications listed.

1. Structurant for Lipid and/or Lipid Phase

The present invention may optionally comprise a lipid structurant. The structurant can provide the dispersed phase with the correct rheological properties. This can aid in providing effective deposition and retention to the skin. The structured lipid phase should have a viscosity in the range of from about 100 to about 200,000 poise measured at 1 $Sec^{-1}$, preferably from about 200 to about 100,000 poise, and even more preferably from about 200 to about 50,000 poise, as determined using the Lipid Rheology Method described below. The amount of structurant required to produce this viscosity will vary depending on the oil and the structurant, but in general, the structurant will preferably be less than 75 weight percent of the dispersed lipid phase, more preferably less than 50 weight percent, and still more preferably less than 35 weight percent of the dispersed lipid phase.

The structurant can be either an organic or inorganic structurant. Examples of organic thickeners suitable for the invention include solid fatty acid esters, natural or modified fats, fatty acid, fatty amine, fatty alcohol, natural and synthetic waxes, and petrolatum, and the block copolymers sold under the name KRATON by Shell. Inorganic structuring agents include hydrophobically modified silica or hydrophobically modified clay. Nonlimiting examples of inorganic structurants include BENTONE 27V, BENTONE 38V or BENTONE GEL MIO V from Rheox; and CAB-O-SIL TS720 or CAB-O-SIL M5 from Cabot Corporation.

Structurants meeting the above requirements with the selected skin compatible oil can form a 3-dimensional network to build up the viscosity of the selected oils. It has been found that such structured lipid phases, i.e., built with the 3-dimensional network, are extremely desirable for use as wet-skin treatment compositions used in bathing. These structured oils can deposit and be retained very effectively on wet skin and retained after rinsing and drying to provide long-lasting after wash skin benefit without causing a too oily/greasy wet and dry feel. It is believed that the highly desirable in-use and after-use properties of such structured oils are due to their shear thinning rheological properties and the weak structure of the network. Due to its high low-shear viscosity, the 3-dimensional network structured oil can stick and retain well on the skin during application of the skin conditioner. After being deposited on the skin, the network yields easily during rubbing due to the weak structuring of the crystal network and its lower high-shear viscosity.

2. Surfactants

A wide variety of surfactants can be useful herein, both for emulsification of the dispersed phase as well as to provide acceptable spreading and in use properties for non-lathering systems. For cleansing applications, the surfactant phase also serves to clean the skin and provide an acceptable amount of lather for the user. The composition preferably contains no more than about 50 weight percent of a surfactant, more preferably no more than about 30 weight percent, still more preferably no more than about 15 weight percent, and even more preferably no more than about 5 weight percent of a surfactant. The composition preferably contains at least about 0.1 weight percent of a surfactant, more preferably at least about 1 weight percent, still more preferably at least about 3 weight percent, and even more preferably at least about 5 weight percent of a surfactant. For cleansing applications the personal care compositions preferably produces a Total Lather Volume of at least 300 ml, more preferably greater than 600 ml as described in the Lathering Volume Test. The personal care compositions preferably produces a Flash Lather Volume of at least 100 ml, preferably greater than 200 ml, more preferably greater than 300 ml as described in the Lathering Volume Test.

In one embodiment, the composition comprises an additional aqueous phase that is a visually distinct phase that is packaged in physical contact with the composition while maintaining stability. The additional aqueous phase may comprise a surfactant. In this embodiment, the hydrophilic liquid, structurant, surface active, and lipid phase may be within the domain of one aqueous phase, while the additional aqueous phase comprises a surfactant. The two aqueous phases (one with the surfactant and one with the hydrophilic liquid, structurant, surface active, and lipid phase) may be visually distinct phases that are packaged in physical contact and maintain stability.

Preferable surfactants include those selected from the group consisting of anionic surfactants, nonionic surfactants, amphoteric surfactants, non-lathering surfactants, emulsifiers and mixtures thereof. Non-limiting examples of surfactants useful in the compositions of the present invention are disclosed in U.S. Pat. No. 6,280,757.

a. Anionic Surfactants

Non-limiting examples of anionic surfactants useful in the compositions of the present invention are disclosed in McCutcheon's, Detergents and Emulsifiers, North American edition (1986), published by allured Publishing Corporation; McCutcheon's, Functional Materials, North American Edition (1992); and U.S. Pat. No. 3,929,678, to Laughlin et al., issued Dec. 30, 1975.

A wide variety of anionic surfactants are useful herein. Non-limiting examples of anionic surfactants include those selected from the group consisting of sarcosinates, sulfates, isethionates, taurates, phosphates, lactylates, glutamates, and mixtures thereof. Amongst the isethionates, the alkoyl isethionates are preferred, and amongst the sulfates, the alkyl and alkyl ether sulfates are preferred.

Other anionic materials useful herein are fatty acid soaps (i.e., alkali metal salts, e.g., sodium or potassium salts) typically from a fatty acid having from about 8 to about 24 carbon atoms, preferably from about 10 to about 20 carbon atoms. These fatty acids used in making the soaps can be obtained from natural sources such as, for instance, plant or animal-derived glycerides (e.g., palm oil, coconut oil, soybean oil, castor oil, tallow, lard, etc.) The fatty acids can also be synthetically prepared. Soaps and their preparation are described in detail in U.S. Pat. No. 4,557,853.

Other anionic materials include phosphates such as monoalkyl, dialkyl, and trialkylphosphate salts. Non-limiting examples of preferred anionic lathering surfactants useful herein include those selected from the group consisting of sodium lauryl sulfate, ammonium lauryl sulfate, ammonium laureth sulfate, sodium laureth sulfate, sodium trideceth sulfate, ammonium cetyl sulfate, sodium cetyl sulfate, ammonium cocoyl isethionate, sodium lauroyl isethionate, sodium lauroyl lactylate, triethanolamine lauroyl lactylate, sodium caproyl lactylate, sodium lauroyl sarcosinate, sodium myristoyl sarcosinate, sodium cocoyl sarcosinate, sodium lauroyl methyl taurate, sodium cocoyl methyl taurate, sodium lauroyl glutamate, sodium myristoyl glutamate, and sodium cocoyl glutamate and mixtures thereof.

Especially preferred for use herein are ammonium lauryl sulfate, ammonium laureth sulfate, sodium lauroyl sarcosinate, sodium cocoyl sarcosinate, sodium myristoyl sarcosinate, sodium lauroyl lactylate, and triethanolamine lauroyl lactylate.

b. Non-Ionic Surfactants

Non-limiting examples of nonionic surfactants for use in the compositions of the present invention are disclosed in McCutcheon's, Detergents and Emulsifiers, North American edition (1986), published by allured Publishing Corporation; and McCutcheon's, Functional Materials, North American Edition (1992).

Nonionic surfactants useful herein include those selected from the group consisting of alkyl glucosides, alkyl polyglucosides, polyhydroxy fatty acid amides, alkoxylated fatty acid esters, sucrose esters, amine oxides, and mixtures thereof.

Non-limiting examples of preferred nonionic surfactants for use herein are those selected from the group consisting of $C_8$-$C_{14}$ glucose amides, $C_8$-$C_{14}$ alkyl polyglucosides, sucrose cocoate, sucrose laurate, lauramine oxide, cocoamine oxide and mixtures thereof.

c. Amphoteric Surfactants

The term "amphoteric surfactant," as used herein, is also intended to encompass zwitterionic surfactants, which are well known to formulators skilled in the art as a subset of amphoteric surfactants.

A wide variety of amphoteric lathering surfactants can be used in the compositions of the present invention. Particularly useful are those which are broadly described as derivatives of aliphatic secondary and tertiary amines, preferably wherein the nitrogen is in a cationic state, in which the aliphatic radicals can be straight or branched chain and wherein one of the radicals contains an ionizable water solubilizing group, e.g., carboxy, sulfonate, sulfate, phosphate, or phosphonate.

Non-limiting examples of amphoteric surfactants useful in the compositions of the present invention are disclosed in McCutcheon's, Detergents and Emulsifiers, North American edition (1986), published by allured Publishing Corporation; and McCutcheon's, Functional Materials, North American Edition (1992).

Non-limiting examples of zwitterionic surfactants include those selected from the group consisting of betaines, sultaines, hydroxysultaines, alkyliminoacetates, iminodialkanoates, aminoalkanoates, and mixtures thereof.

Preferred surfactants for use herein include the following, wherein the anionic surfactant is selected from the group consisting of ammonium lauroyl sarcosinate, sodium trideceth sulfate, sodium lauroyl sarcosinate, ammonium laureth sulfate, sodium laureth sulfate, ammonium lauryl sulfate, sodium lauryl sulfate, ammonium cocoyl isethionate, sodium cocoyl isethionate, sodium lauroyl isetlionate, sodium cetyl sulfate, sodium lauroyl lactylate, triethanolamine lauroyl lactylate, and mixtures thereof, wherein the non-ionic surfactant is selected from the group consisting of lauramine oxide, cocoamine oxide, decyl polyglucose, lauryl polyglucose, sucrose cocoate, $C_{12-14}$ glucosamides, sucrose laurate, and mixtures thereof; and wherein the amphoteric surfactant is selected from the group consisting of disodium lauroamphodiacetate, sodium lauroamphoacetate, cetyl dimethyl betaine, cocoamidopropyl betaine, cocoamidopropyl hydroxy sultaine, and mixtures thereof.

d. Non-Lathering Surfactants

A wide variety of non-lathering surfactants are useful herein. The composition of the present invention can comprise a sufficient amount of one or more non-lathering surfactants to emulsify the dispersed phase to yield an appropriate particle size and good application properties on wet skin.

Nonlimiting examples of these non-lathering compositions are: polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate, Polysorbate 60, glyceryl stearate, PEG-100 stearate, polyoxyethylene 20 sorbitan trioleate (Polysorbate 85), sorbitan monolaurate, polyoxyethylene 4 lauryl ether sodium stearate, polyglyceryl-4 isostearate, hexyl laurate, steareth-20, ceteareth-20, PPG-2 methyl glucose ether distearate, ceteth-10, diethanolamine cetyl phosphate, glyceryl stearate, PEG-100 stearate, and mixtures thereof.

e. Emulsifier Systems

In addition, there are several emulsifier mixtures that are useful in some embodiments. Examples include PROLIPID 141 (glyceryl stearate, behenyl alcohol, palmitic acid, stearic acid, lecithin, lauryl alcohol, myristyl alcohol and cetyl alcohol) and 151 (Glyceryl stearate, cetearyl alcohol, stearic acid, 1-propanamium, 3-amino-N-(2-(hydroxyethyl)-N—N-Dimethyl,N—C(16-18) Acyl Derivatives, Chlorides) from ISP; POLAWAX NF (Emulsifying wax NF), and INCROQUAT BEHENYL TMS (behentrimonium sulfate and cetearyl alcohol) from Croda; and EMULLIUM DELTA (cetyl alcohol, glyceryl stearate, peg-75 stearate, ceteth-20 and steareth-20) from Gattefosse.

3. Cationic Polymers

The present invention may also contain organic cationic deposition polymer Concentrations of the cationic deposition polymer preferably range from about 0.025% to about 3%, more preferably from about 0.05% to about 2%, even more preferably from about 0.1% to about 1%, by weight of the personal care composition.

Suitable cationic deposition polymers for use in the present invention contain cationic nitrogen-containing moieties such as quaternary ammonium or cationic protonated amino moieties. The cationic protonated amines can be primary, secondary, or tertiary amines (preferably secondary or tertiary), depending upon the particular species and the selected pH of the personal cleansing composition. The average molecular weight of the cationic deposition polymer is between about 5,000 to about 10 million, preferably at least about 100,000, more preferably at least about 200,000, but preferably not more than about 2 million, more preferably not more than about 1.5 million. The polymers also have a cationic charge density ranging from about 0.2 meq/gm to about 5 meq/gm, preferably at least about 0.4 meq/gm, more preferably at least about 0.6 meq/gm, at the pH of intended use of the personal cleansing composition, which pH will generally range from about pH 4 to about pH 9, preferably from about pH 5 and about pH 8.

Nonlimiting examples of cationic deposition polymers for use in the personal care composition include polysaccharide polymers, such as cationic cellulose derivatives. Preferred cationic cellulose polymers are the salts of hydroxyethyl cellulose reacted with trimethyl ammonium substituted epoxide, referred to in the industry (CTFA) as Polyquaternium 10 which are available from Amerchol Corp. in their Polymer KG, JR and LR series of polymers, with a preferred being KG-30M.

Other suitable cationic deposition polymers include cationic guar gum derivatives, such as guar hydroxypropyltrimonium chloride, specific examples of which include the Jaguar series (preferably Jaguar C-17) commercially available from Rhodia Inc., and N-Hance polymer series commercially available from Aqualon.

Other suitable cationic deposition polymers include synthetic cationic polymers. The cationic polymers suitable for use in the cleansing composition herein are water soluble or dispersible, non crosslinked, cationic polymers having a cationic charge density of from about 4 meq/gm to about 7 meq/gm, preferably from about 4 meq/gm to about 6 meq/gm, more preferably from about 4.2 meq/gm to about 5.5 meq/gm. The select polymers also may have an average molecular weight of from about 1,000 to about 1 million, preferably from about 10,000 to about 500,000, more preferably from about 75,000 to about 250,000.

The concentration of the cationic polymer in the personal care composition ranges from about 0.025% to about 5%, preferably from about 0.1% to about 3%, more preferably from about 0.2% to about 1%, by weight of the composition.

A non limiting example of a commercially available synthetic cationic polymer for use in the cleansing compositions is polymethyacrylamidopropyl trimonium chloride, available under the trade name POLYCARE 133, from Rhodia.

4. Other Optional Ingredients

Other non limiting examples of optional ingredients include benefit agents that are selected from the group consisting of vitamins and derivatives thereof (e.g., ascorbic acid, vitamin E, tocopheryl acetate, and the like); sunscreens; thickening agents (e.g., polyol alkoxy ester, available as CROTHIX from Croda); preservatives for maintaining the anti microbial integrity of the cleansing compositions; anti acne medicaments (resorcinol, salicylic acid, and the like); antioxidants; skin soothing and healing agents such as aloe vera extract, allantoin and the like; chelators and sequestrants; and agents suitable for aesthetic purposes such as fragrances, essential oils, skin sensates, pigments, pearlescent agents (e.g., mica and titanium dioxide), lakes, colorings, and the like (e.g., clove oil, menthol, camphor, eucalyptus oil, and eugenol), antibacterial agents and mixtures thereof. These materials can be used at ranges sufficient to provide the required benefit, as would be obvious to one skilled in the art.

Method of Use

The personal care compositions of the present invention are preferably applied topically to the desired area of the skin or hair in an amount sufficient to provide effective delivery of the product. The compositions can be applied directly to the skin or hair or indirectly via the use of a cleansing puff, washcloth, sponge or other implement. The compositions may be in the form of a body wash, shampoo, conditioner, moisture rinse, mousse, substrate, etc. The compositions are preferably diluted with water prior to, during, or after topical application, and then subsequently the skin or hair rinsed or dried off, preferably rinsed off of the applied surface using water or a water-insoluble substrate in combination with water.

The present invention is therefore also directed to methods of cleansing the skin through the above-described application of the compositions of the present invention. The methods of the present invention are also directed to a method of providing effective delivery of the desired skin benefit agent, and the resulting benefits from such effective delivery as described herein, to the applied surface through the above-described application of the compositions of the present invention.

Compositions of the present invention may deposit at least about 1 µg/cm$^2$ of said hydrophilic liquid on skin according to the in-vivo deposition method when the concentration of the hydrophilic liquid is at least about 0.5% of the composition, preferably at least about 1% of the composition, more preferably at least about 5% of the composition. Compositions comprising less than 0.5% of the hydrophilic liquid may also deposit at least about 1 µg/cm$^2$ of said hydrophilic liquid.

The present invention may also be useful in rinse-off applications other than personal care compositions including pet care, auto care, home care and medical applications.

Method of Making

The personal care compositions of the present invention may be prepared by any known or otherwise effective technique suitable for making and formulating emulsions and dispersions. It is especially effective to use slow mixing techniques for mixing the hydrophilic liquids with a structurant, mixing the structured hydrophilic liquid with a surface active, and then mixing with the lipid. Non-limiting mixing techniques include hand mixing or mixing with mechanical mixers. For association structure forming compositions, it may be necessary to allow the structured hydrophilic liquids to sit for a few hours to form the structures. Higher speed mixing is used for mixing the lipid phase with the aqueous phase. Generally, the compositions are prepared at ambient temperature/room temperature. The association structure forming process will depend on the physical state of the surface active. If the surface active is a solid or semisolid at ambient temperature, it may be heated to melt and mixed with the hydrophilic liquid and allowed to cool to ambient temperature.

Analytical Methods

1. Lipid Rheology Method

Lipid rheology is measured on a TA Instruments AR2000 stress-controlled rheometer with a Peltier temperature controlled sample stage or an equivalent. A parallel plate geometry is used with a 40 mm plate and a 1 mm gap. The lower plate is heated to 85° C. and the melted lipid and structurant (if present) is added onto the lower plate and allowed to equilibrate. The upper plate is then lowered to the 1 mm gap while ensuring the lipid fills the gap fully, [spinning the top plate and adding more lipid to promote wicking], and the sample is cooled quickly to 25° C. and equilibrated at 25° C. for 5 minutes. Viscosity is then measured using a stress-ramp procedure common on these types of machines using a logarithmic stress ramp from 20 to 2000 Pa at a rate of 60 seconds per decade (2 minute ramp test), with 20 measurements points per decade. The starting and ending stress is sufficient to induce flow and reach a shear rate of at least 10 sec−1. Viscosity is recorded and the data fitted to a power law model using Equation 1. Only points between 0.001 sec−1 and 40 seconds−1 are to be used in the power law fit. The viscosity at 1.0 sec−1 is calculated from Equation 1. One should carefully watch the sample during the test so that when the material is ejected from under the plate, the method is stopped.

Viscosities are recorded and the data fit to a power law with the following Equation 1:

$$\eta = \kappa \cdot \gamma(dot)^{(n-1)}$$

where $\eta$=viscosity, $\kappa$ is the consistency and $\gamma$ (dot) is the shear rate, and n is the shear index. The viscosity at 1 sec−1 is then calculated using the calculated values of $\kappa$ and n from the fitted data.

2. Stability Agent Viscosity Test

Polymeric stabilizer phase is formed using the ratio of stabilizer to water that will be found in the particular formulation of interest. For example, if the formulation contains 3 parts stabilizing polymer and 72 parts water, the ratio will be 1:24. The polymer is hydrated in the water phase at the appropriate ratio. The method of hydration will vary depending upon the polymer type, and may require high shear, heating, and/or neutralization. In any event, the polymer should be properly hydrated according to manufacturer's instructions. Once the polymer is fully hydrated, the system is allowed to sit at room temperature for at least 24 hours. After the resting period, the viscosity of the stabilizer phase is measured with a Brookfield or similar viscometer using a cone and plate (Spindle 41 for a Brookfield model DV II+) geometry at 1 sec−1 and 25° C. 2 ml of the product is placed in the cup of the viscometer and attached to the unit. The rotation is started and after 2 minutes the viscosity is recorded.

3. Lather Volume

Lather volume of a personal care composition can be measured using a graduated cylinder and a tumbling apparatus. A 1,000 ml graduated cylinder is chosen which is marked in 10 ml increments and has a height of 14.5 inches at the 1,000 ml mark from the inside of its base (for example, Pyrex No. 2982). Distilled water (100 grams at 23° C.) is added to the graduated cylinder. The cylinder is clamped in a rotating device, which clamps the cylinder with an axis of rotation that transects the center of the graduated cylinder. One gram of the total personal care composition is added into the graduated cylinder and the cylinder is capped. The cylinder is rotated at a rate of 10 revolutions in about 20 seconds, and stopped in a vertical position to complete the first rotation sequence. A timer is set to allow 30 seconds for the lather thus generated to drain. After 30 seconds of such drainage, the first lather volume is measured to the nearest 10 ml mark by recording the lather height in ml up from the base (including any water that has drained to the bottom on top of which the lather is floating).

If the top surface of the lather is uneven, the lowest height at which it is possible to see halfway across the graduated cylinder is the first lather volume (ml). If the lather is so coarse that a single or only a few foam cells ("bubbles") reach across the entire cylinder, the height at which at least 10 foam cells are required to fill the space is the first lather volume, also in ml up from the base. Foam cells larger than one inch in any dimension, no matter where they occur, are designated as unfilled air instead of lather. Foam that collects on the top of the graduated cylinder but does not drain is also incorporated in the measurement if the foam on the top is in its own continuous layer, by adding the ml of foam collected there using a ruler to measure thickness of the layer, to the ml of foam measured up from the base. The maximum foam height is 1,000 ml (even if the total foam height exceeds the 1,000 ml mark on the graduated cylinder). One minute after the first rotation is completed, a second rotation sequence is commenced which is identical in speed and duration to the first rotation sequence. The second lather volume is recorded in the same manner as the first, after the same 30 seconds of drainage time. A third sequence is completed and the third lather volume is measured in the same manner, with the same pause between each for drainage and taking the measurement.

The lather result after each sequence is added together and the Total Lather Volume determined as the sum of the three measurements, in ml. The Flash Lather Volume is the result after the first rotation sequence only, in ml, i.e., the first lather volume.

4. Contact Angle Method

Use a hydrophobic [polyethylene terephthalate (PET)] and hydrophilic [aluminum foil] surface to evaluate the wettability of a given substance on either substrate. Determine the static contact angles on a flat, smooth, clean piece of either aluminum foil (UHV Foil from All Foils) or PET (Scotchpak 1022 from 3M) 3 times with Millipore Milli-Q plus purified distilled water and 99% pure diiodomethane (Sigma Aldrich) in a constant temperature (25±1 C) and constant humidity (relative humidity of 45±2%) clean room (positive pressure, air filtered). The contact angle method is described below. Determine the contact angles of water and diiodomethane (DIM) (1) on flat, smooth pieces of aluminum foil and PET from pieces carefully removed from the packaging without contaminating the surfaces; (2) after rinsing the pieces 3 times with Millipore purified distilled water and blow drying with ultra-pure (99.999%) nitrogen gas; and (3) after rinsing pieces 3 times with 99% pure toluene and blow drying with ultra-pure nitrogen gas. The Pet or aluminum foil is clean if all three determinations of contact angle agree to the following: (1) on PET: greater or equal to 88° for water and less than or equal to 45 for DIM and (2) on Aluminum Foil: less than or equal to 41° for water and greater than or equal to 39° for DIM, and (3) there is no more than a 2-3 degree variance in the 3 sets of pooled measurements on PET or aluminum foil. The surfaces of the aluminum foil and PET must be flat, smooth, chemically inert (does not dissolve, swell within 30 minutes when in contact with liquids being tested), and chemically homogeneous (functional groups are uniformly dispersed across surface).

Use a Dynamic Contact Angle Analyzer (FTÅ 200, First Ten Angstroms, Portsmouth, Va.). Use the equipment in a clean room kept at 25±1 degree C. and 45±2% relative humidity on a vibration free bench. Load Millipore purified distilled water or 99% pure diiodomethane in aseptic chemically uncontaminated 10 mL syringes with a 27 gauge aseptic, non-chemically contaminated stainless steel blunt tip needles. Mount the syringe in the vertical position with the needle pointing down. Dangle 7±1 µL of water or 4±1 µL of DIM from the tip of the needle using the pump controls of FTÅ 200. Carefully lay a flat, smooth piece of PET or aluminum foil on the z-stage directly below the needle. Use the z-stage to carefully and slowly raise the surface of the PET or aluminum foil until it gently touches the bottom of the dangling drop. Illuminate the rear light to 80%. Acquire a focused image of the drop at a 3 degree incline (look down) to the plane of the PET or aluminum foil. Acquire the image after the drop equilibrated (stopped spreading on the surface) or at 30 minutes for the highly viscous materials (>20,000 cSt). Determine an aspherically fitted contact angle for both sides of the drop. Report the average value for both sides. Repeat the contact angle determinations 3 times on separate sections of aluminum foil or PET for each compound tested.

TABLE 1

Examples of contact angles of compounds determined on aluminum foil and PET.

| Compound | Contact Angle (degrees) | |
| --- | --- | --- |
| | Aluminum Foil | PET |
| Lecithin | 20.3 | 18.9 |
| Abil EM 90 | 10.9 | 18.5 |
| Silicone 200 Fluid, 5,000 cSt | 11.6 | 27.7 |
| Silicone 200 Fluid, 330,000 cSt | 28.3 | 36.0 |
| Aminosilicone TSF 4707 | 14.8 | 17.8 |
| Isopropyl myristate | 13.8 | 13.2 |

If the material exiting the needle does not form a drop but retains the shape of the orifice of the needle, then the material is spread into an even, smooth, thick (1-2 mm) film on a glass microscope slide. 4-µL of 99% pure DIM and 7-µL Millipore purified distilled water are applied to the film in a manner identical to the method describing the determination of contact angles on PET or aluminum foil above. Static contact angles for DIM and water spreading on the films are determined after the fluids have stopped spreading—usually within 30 seconds.

5. In-Vivo Deposition Method for Hydrophilic Actives

Method for measuring hydrophilic actives on skin—apply product containing hydrophilic benefit agent (analyte) to the inner forearm according to the following procedure:

Rinse the forearm from the elbow to the wrist for 5 seconds using 35° C. city water at a flow rate of 50-60 mL/sec. Apply 1.0 mL of liquid soap or the lather from a wetted soap bar rotated in both hands for 6 full rotations to the entire inner forearm using 10 full back and forth strokes. Rinse the lather from the forearm for 10 seconds. Rub 1.0 mL of product onto the inner forearm for 10 seconds. Leave the product on the forearm for 10 seconds. Rinse the forearm with water for 10 seconds. Gently pat the forearm dry with a clean, dry paper towel.

Recover deposited analyte from the forearm by using the following tape-stripping procedure. Firmly place D-Squame tape (22-mm diameter, CuDerm Corporation) on the inner forearm at least 2 inches from the elbow crease. Remove the tape strip with clean Teflon-coated tweezers and place in its own individual pre-labeled container (e.g., a disposable petri dish) with the adhesive side of the tape facing up. Place subsequent tapes firmly on the same spot and collect in the same manner until a total of 10 tapes are collected per site. Extract additional areas and pool if necessary to meet the sensitivity limits of the chromatography or electrophoretic method.

Use extraction solvent(s) to quantitatively extract (greater than or equal to 95% recovery) the analyte from the tape. Use either (1) a single solvent or solution of miscible solvents to extract the analyte from the 10 tapes pooled in a container without also extracting components from the adhesive which interfere with the analyte or internal standard bands in the chromatography or electrophoresis or (2) use 2 or more immiscible solvents or solutions of solvents which both extract the analyte from the tape and partition the analyte in a phase separate from the components of the adhesive that interfere with the analyte or internal standard bands used in the chromatography or electrophoresis described below. Employ sonication or vibration to improve analyte extraction. If the analyte is not lost or decomposed, several collection sites can be pooled and concentrated by evaporation at ambient, sub-ambient, or elevated temperature with or without a vacuum, or with or without a greater than or equal to 99.999% pure gas blow down in order to increase the total amount of analyte recovered.

Use a chromatography or capillary electrophoretic system with appropriate detector that produces adequate sensitivity (signal to noise ratio greater than or equal to 10 for analyte levels at the levels extracted from skin) and selectivity (baseline resolution, or no mass/charge band overlap or no radioactive counting interference—depending on the type of detector employed) between the analyte or internal standard bands and other bands associated with the components from the skin, tape strip adhesive, or product in order to accurately quantitate the analyte (greater than or equal to 95% confidence limit) when the instrument is functioning properly (passes system suitability criteria from the manufacturer's operating instructions or the current USP (U.S. Pharmacopeia) for chromatographic methods). Sensitivity for the analytes should be 80-120% of the levels deposited on the skin. Internal standards are compounds with similar chemical and physical properties to the hydrophilic benefit agent(s) which (1) do not coelute or interfere with mass/charge bands or interfere with the radioactive counting of the hydrophilic benefit agent bands; and (2) elute close to the hydrophilic benefit agent bands. Proper functioning would also produce the following 2 conditions if present in the chromatographic or electrophoretic system: (1) The % RSD (relative standard deviation) of the retention time is less than or equal to 2.0% for six sequential injections of the analyte(s) and internal standard; and (2) a minimum correlation coefficient between analyte band response (normalized to internal standard) and concentration of analyte of 0.99 for a minimum of 5 point external calibration curve. Two examples of chromatographic methods are given below:

EXAMPLE 1

Glycerin as the Hydrophilic Benefit Agent

Add 1 mL of 0.01 N aqueous $H_2SO_4$ and 9 mL methanol to the container containing the tape strips, vortex for 1 minute, sonicate for 10 minutes, allow to stand for 30 minutes, and filter using a 0.45 µm pore syringe filter. Concentrate the filtrate using a gentle nitrogen purge to 1 mL total volume. Use a high performance liquid chromatography (HPLC, Model 2595, Waters Corp., Milford, Mass.) with a differential refractometer detector (Model 2414, Waters Corp.) employing the following conditions: IOA-1000 column (300 mm×7.8 mm, Alltech Associates, Inc, Deerfield, Ill.) at 65° C. with an isocratic flow rate at 0.6 ml min$^{-1}$ of 0.01 N aqueous $H_2SO_4$ and 10 μL injection volume.

EXAMPLE 2

Dihydroxyacetone as the Hydrophilic Benefit Agent

Add 1 mL of 0.005 N aqueous $H_2SO_4$ and 9 mL methanol to the container containing the tape strips, vortex for 1 minute, sonicate for 10 minutes, allow to stand for 30 minutes, and filter using a 0.45 μm pore syringe filter. Concentrate the filtrate using a gentle nitrogen purge to 1 mL total volume. Use an HPLC (Model 2595, Waters Corp.) with a differential refractometer detector (Model 2414, Waters Corp.) employing the following conditions: IOA-1000 column (300 mm×7.8 mm, Alltech Associates, Inc.) at 65° C. with an isocratic flow rate at 0.6 ml min$^-$ of 0.005 N aqueous $H_2SO_4$ and 40 μL injection volume.

6. Identification of Association Structures

Association structure formation may be identified using one or more of several identification techniques. The onset of association structure formation and the occurrence of a substantially one-phase liquid crystal state for a particular surface active and hydrophilic liquid system can be identified by: 1) visual observation with the naked eye; 2) birefringent optical activity observed by polarized light microscopy; 3) measurement of the surface active/hydrophilic liquid system NMR spectra; 4) measurement of apparent viscosity profile; 5) presence of a characteristic "texture" pattern observable under cryo Scanning Electron Microscopy (cryo-SEM) and/or Freeze-Fractured Transmission Electron Microscopy (FF-TEM); 6) x-ray diffraction. These methods are described in more detail in U.S. Pat. No. 5,599,555.

NON-LIMITING EXAMPLES

The compositions illustrated in the following Examples exemplify specific embodiments of the compositions of the present invention, but are not intended to be limiting thereof. Other modifications can be undertaken by the skilled artisan without departing from the spirit and scope of this invention. These exemplified embodiments of the composition of the present invention provide enhanced deposition of the personal care composition. The compositions illustrated in the following Examples are prepared by conventional formulation and mixing methods, an example of which is described above. All exemplified amounts are listed as weight percents and exclude minor materials such as diluents, preservatives, color solutions, imagery ingredients, botanicals, and so forth, unless otherwise specified.

| Ingredient | Ex. 1 wt % | Ex. 2 wt % | Ex. 3 wt % | Ex. 4 wt % | Ex. 5 wt % | Ex. 6 wt % | Ex. 7 wt % | Ex. 8 wt % | Ex. 9 wt % | Ex. 10 wt % |
|---|---|---|---|---|---|---|---|---|---|---|
| I. Aqueous Phase Composition | | | | | | | | | | |
| Hydroxypropyl Starch Phosphate (Structure XL from National Starch) | 3.5 | 4.0 | 3.5 | 3.5 | 3.5 | 3.0 | 3.5 | 3.5 | 3.5 | 3.5 |
| Emulsifying Wax NF (Polawax from Croda) | 2.75 | 3.0 | 2.75 | | 2.75 | 2.5 | | 2.75 | 2.75 | 2.75 |
| Behenetrimonium methosulfate and cetearyl alcohol (Incroquat Behenyl TMS from Croda) | | | | 2.25 | | | 2.0 | | | |
| Fragrance | 1.0 | 1.0 | 1.0 | 1.0 | 1.0 | 1.0 | 1.0 | 1.0 | 1.0 | 1.0 |
| Preservatives | 0.8 | 0.8 | 0.8 | 0.8 | 0.8 | 0.8 | 0.8 | 0.8 | 0.8 | 0.8 |
| Water | Q.S. | Q.S. | Q.S. | Q.S. | Q.S. | Q.S. | Q.S. | Q.S. | Q.S. | Q.S. |
| II. Lipid Composition | | | | | | | | | | |
| Petrolatum (Superwhite Protopet from WITCO) | 12 | 20 | 12 | 14 | 24 | 15 | 20 | 13 | | 20 |
| Mineral Oil (Hydrobrite 1000 PO White MO from WITCO) | | 10 | | | | 2 | | | 13 | |
| III. Structured Hydrophilic Phase Composition | | | | | | | | | | |
| Dimethicone Fluid (Dow Corning Silicone Fluid 60,000 cst) | | 1.2 | | | | | | | | |
| Lecithin Thermolec ™ 200 (ADM Specialty Ingredients) | 9.0 | | | 10 | 8 | 10 | | | | |
| Monomuls 90 L-12 (Cognis Co.) | | | | | | | | 3.5 | 1.5 | |
| Monomuls 90-O18 (Cognis Co.) | | | | | | | | 3.5 | 1.5 | 3.0 |
| Generol 122 N E-5 (Cognis Co.) | | | | | | | | | | 3.0 |
| Abil EM 90 (Degussa) | | | | 9.0 | | | | | | |

-continued

| Ingredient | Ex. 1 wt % | Ex. 2 wt % | Ex. 3 wt % | Ex. 4 wt % | Ex. 5 wt % | Ex. 6 wt % | Ex. 7 wt % | Ex. 8 wt % | Ex. 9 wt % | Ex. 10 wt % |
|---|---|---|---|---|---|---|---|---|---|---|
| Silica Shells (KOBO products) | 1.2 | 1.0 | 1.2 | | | | | | | |
| Hubersorb 600 (J. M. Huber Corporation) | | | | 1.5 | | | | | | |
| Water Lock G-580 (Grain Processing Corporation | | | | | 1.2 | | | | | |
| Zil Gel SM (Presperse Incorporated) | | | | | | | 8.0 | | | |
| Kosher Superol Glycerin (Procter & Gamble Co.) | 7.8 | 8.1 | 7.8 | 7.5 | 4.2 | | 7.0 | 7.0 | 8.0 | 7.0 |
| Niacinamide | | | | | | | | | 5.5 | |
| Water | | | | | 4.2 | | | | | |

| Ingredient | Ex. 11 wt % | Ex. 12 wt % |
|---|---|---|
| I. Aqueous Phase Composition | | |
| Hydroxypropyl Starch Phosphate (Structure XL from National Starch) | 3.5 | 3.5 |
| Emulsifying Wax NF (Polawax from Croda) | 2.75 | 2.75 |
| Behenetrimonium methosulfate and cetearyl alcohol (Incroquat Behenyl TMS from Croda) | | |
| Fragrance | 1.0 | 1.0 |
| Preservatives | 0.8 | 0.8 |
| Water | Q.S. | Q.S. |
| II. Lipid Composition | | |
| Petrolatum (Superwhite Protopet from WITCO) | 20 | 19 |
| Mineral Oil (Hydrobrite 1000 PO White MO from WITCO) | | |
| III. Structured Hydrophilic Phase Composition | | |
| General 122 N E-5 (Cognis Co.) | 1.1 | 3.0 |
| Monomuls 90 L-12 (Cognis Co.) | 3.0 | |
| Monomuls 90-O18 (Cognis Co.) | 2.0 | |
| Kosher Superol Glycerin (Procter & Gamble Co.) | | 1.0 |
| Dihydroxyacetone (Merck KGaA) | 5.5 | 5.5 |
| Water | 3.0 | 2.1 |

Prepare the personal care composition of Examples 1-12 by conventional formulation and mixing techniques.

Prepare the aqueous phase composition by first dispersing the hydroxypropyl starch phosphate in water. Add emulsifying wax and heat to 160° F. (71.1° C.). Next, place the mixing vessel in a water bath to cool to under 100° F. (37.78° C.). Add fragrance.

Prepare the structured hydrophilic phase by first premixing the hydrophilic liquid with the structurant if necessary (i.e. not already pre-mixed by the supplier). Mix the mixture with the surface active.

Mix the structured hydrophilic phase with the lipid. If the lipid is a solid or semi-solid, it is preferable to add the internal structured hydrophilic phase to melt lipid.

Add the premix of the lipid phase to the aqueous phase and mix via conventional mixing techniques.

EXAMPLES 13-14

| Ingredient | Ex 13 wt % | Ex 14 wt % |
|---|---|---|
| I. Cleansing Phase Composition | | |
| Miracare SLB-365 (from Rhodia) (Sodium Trideceth Sulfate, Sodium Lauramphoacetate, Cocamide MEA) | 47.4 | 47.4 |
| Guar Hydroxypropyltrimonium Chloride (N-Hance 3196 from Aqualon) | 0.7 | 0.7 |
| PEG 90M (Polyox WSR 301 from Dow Chemical) | 0.2 | 0.2 |
| Sodium Chloride | 3.5 | 3.5 |
| Preservatives | 0.84 | 0.84 |
| Citric Acid | 0.4 | 0.4 |
| Perfume | 2.0 | 2.0 |
| Expancel 091 DE 40 d30 (from Expancel, Inc.) | 0.4 | 0.4 |
| Water | Q.S. | Q.S. |
| (pH) | (6.0) | (6.0) |
| II. Lipid Composition | | |
| Petrolatum (Superwhite Protopet from WITCO) | 62.4 | 62.4 |
| Mineral Oil (Hydrobrite 1000 PO White MO from WITCO) | 20.8 | 20.8 |
| III. Structured hydrophilic phase composition | | |
| Lecithin Thermolec ™ 200 (ADM Specialty Ingredients) | 8.0 | |
| Silica Shells (KOBO products) | 1.0 | |
| Monomuls 90 L-12 (Cognis Co.) | | 3.5 |
| Monomuls 90-O18 (Cognis Co.) | | 3.5 |
| Kosher Superol Glycerin (Procter & Gamble Co.) | 7.8 | 10.0 |

Prepare the composition described above by conventional formulation and mixing techniques. Prepare the cleansing phase composition by first adding citric acid into water at a 1:3 ratio to form a citric acid premix. Add the following ingredients into the main mixing vessel in the following sequence: water, Miracare SLB-354, sodium chloride, and preservatives. Start agitation of the main mixing vessel. In a separate mixing vessel, disperse polymer (N-Hance 3196) in water at 1:10 ratio to form a polymer premix. Add the completely dispersed polymer premix into the main mixing vessel with continuous agitation. Disperse PEG 90M (Polyox WSR 301) in water and then add to the main mixing vessel. Then, add the rest of the water, perfume, and Expancel into the batch. Keep agitating until a homogenous solution forms.

Prepare the structured hydrophilic phase by first premixing the hydrophilic liquid with the structurant if necessary (i.e. not already pre-mixed by the supplier). Mix the mixture with the surface active.

Prepare the lipid phase by adding petrolatum into a mixing vessel. Heat the vessel to 190° F. (87.78° C.). Then, add mineral oil with agitation. Add the structured hydrophilic phase with agitation.

The cleansing and lipid phases are density matched to within 0.05 g/cm$^3$. Package both phases into a single container using conventional toothpaste-tube filler equipment. The sample stage spins the bottle during filling process to create a striped appearance. The stripe size is about 6 mm in width and 100 mm in length.

EXAMPLE 15

| Ingredient | wt % |
| --- | --- |
| I. Phase 1 | |
| Ammonium Laureth-3 Sulfate (25% Active) | 46.7 |
| Citric Acid Anhydrous | 1.76 |
| Sodium Lauroamphoacetate (27%) | 43.47 |
| Trihydroxystearin (Thixcin R from Rheox) | 2.35 |
| Preservatives | 1.73 |
| Lauric Acid | 2.35 |
| Petrolatum | 1.64 |
| II. Phase 2 | |
| Ammonium Laureth-3 Sulfate | 18 |
| Ammonium Lauryl Sulfate (25% Active) | 12 |
| Phase 1 | 42.6 |
| Fragrance | 1.0 |
| Premix 1 | |
| Guar Hydroxypropyltrimonium Chloride (N-Hance 3196 from Aqualon) | 0.3 |
| Water | QS |
| Premix 2 | |
| Petrolatum | 15 |
| Monomuls 90-O18 (Cognis Co.) | 4 |
| Kosher Superol Glycerin (Procter & Gamble Co.) | 7 |

Prepare the composition described above by conventional formulation and mixing techniques. Prepare phase 1 by first adding citric acid into the ammonium laureth-3 sulfate. Once the citric acid is full dissolved, add the sodium lauroamphoacetate. Heat the mixture to 190-195° F. Incorporate the trihydroxystearin fully and then add preservatives. Continue to mix as petrolatum is added. Prepare phase 2 in a separate mixing vessel. Add ammonium laureth-3 sulfate then ammonium lauryl sulfate to mixing vessel in a water bath. To this vessel add Phase 1 with continuous mixing. Premix the guar hydroxypropyl trimonium chloride and water (Premix 1). Add Premix 1 to mixing vessel. Prepare premix 2 by mixing petrolatum and the premix of Monomuls 90-O18 with glycerin in a separate mixing vessel. Heat the vessel to 190° F. Then, add Premix 2 to Phase 2. Then add perfume. Keep agitating until a homogenous solution forms.

EXAMPLES 16-18

| Ingredient | Example 16 wt % | Example 17 wt % | Example 18 wt % |
| --- | --- | --- | --- |
| I. Additional Aqueous Phase Composition | | | |
| Miracare SLB-365 (from Rhodia) (Sodium Trideceth Sulfate, Sodium Lauramphoacetate, Cocamide MEA) | 47.4 | 47.4 | 47.4 |
| Cocamide MEA | 3.0 | 3.0 | 3.0 |
| Guar Hydroxypropyltrimonium Chloride (N-Hance 3196 from Aqualon) | 0.7 | 0.7 | 0.7 |
| PEG 90M (Polyox WSR 301 from Dow Chemical) | 0.2 | 0.2 | 0.2 |
| Glycerin | 0.8 | 0.8 | 0.8 |
| Sodium Chloride | 3.5 | 3.5 | 3.5 |
| Disodium EDTA | 0.05 | 0.05 | 0.05 |
| Glydant | 0.67 | 0.67 | 0.67 |
| Citric Acid | 0.4 | 0.4 | 0.4 |
| Perfume | 2.0 | 2.0 | 2.0 |
| Red 7 Ca Lake (From LCW) | 0.01 | 0.01 | 0.01 |
| Water | Q.S. | Q.S. | Q.S. |
| (pH) | (6.0) | (6.0) | (6.0) |
| II Aqueous phase composition | | | |
| Acrylates/Vinyl Isodecanoate Crosspolymer (Stabylen 30 from 3V) | 1.0 | 1.0 | 1.0 |
| Xanthan gum (Keltrol CGT from CP Kelco) | 1.0 | 1.0 | 1.0 |
| Triethanolamine | 1.5 | 1.5 | 1.5 |
| Sodium Chloride | 3.5 | 3.5 | 3.5 |
| Glydant | 0.37 | 0.37 | 0.37 |
| Water and Minors | Q.S. | Q.S. | Q.S. |
| (pH) | (6.0) | (6.0) | (6.0) |
| III. Lipid Composition | | | |
| Petrolatum (Superwhite Protopet from WITCO) | 10 | 10 | |
| Mineral Oil (Hydrobrite 1000 PO White MO from WITCO) | | | 15 |
| IV. Structured Hydrophilic phase Composition | | | |
| Monomuls 90-O18 (Cognis Co.) | 3.5 | 2.0 | 3.0 |
| Monomuls 90-L12 (Cognis Co.) | 3.5 | 3.0 | |
| Kosher Superol Glycerin (Procter & Gamble Co.) | 7.0 | 5.0 | 7.0 |
| Niacinamide | | 5.5 | |

The compositions described above can be prepared by conventional formulation and mixing techniques. Prepare the additional aqueous phase composition by forming the following premixes: add citric acid into water at 1:1 ratio to form a citric acid premix, add polyox WSR-301 into glycerin at 1:3 ratio to form a polyox-glycerin premix, and add cosmetic pigment into glycerin at 1:20 ratio to form a pigment-glycerin premix and mix well using a high shear mixer. Then, add the following ingredients in the main mixing vessel in the following sequence: water, N-Hance 3196, polyox premix, citric acid premix, disodium EDTA, and Miracare SLB-365. Mix for 30 minutes, then begin heating the batch to approximately 49 degrees C. Add CMEA and mix until homogeneous. Then, cool the batch to ambient temperature and add the following ingredients: sodium chloride, glydant, cosmetic pigment premix and perfume. Mix the batch for 60 minutes. Check pH and adjust pH using citric acid or caustic solution if needed.

Prepare the structured hydrophilic phase by first premixing the hydrophilic liquid with the structurant if necessary (i.e. not already pre-mixed by the supplier). Mix the mixture with the surface active.

Mix the structured hydrophilic phase with the lipid. If the lipid is a solid or semi-solid, it is preferable to add the structured hydrophilic phase to the lipid.

Add the premix of the lipid phase to the aqueous phase and mix via conventional mixing techniques.

Prepare the aqueous phase by slowly adding Stabylene 30 into water with continuous mixing. Then, add Keltrol CG-T. Heat the batch to 85 degrees C. with continuous agitation. Then, add lipid phase containing the structured hydrophilic phase. Cool down the batch to ambient temperature. Then, add Triethanolamine. Add sodium chloride, glydant and mix until homogeneous.

The aqueous phase and the additional aqueous phases can be combined by first placing the separate phases in separate storage tanks having a pump and a hose attached. Then, pump the phases in predetermined amounts into a single combining section. Next, move the phases from the combining sections into the blending sections and mix the phases in the blending section such that the single resulting product exhibits a distinct pattern of the phases, including but not limited to, striped, marbled, geometric, and mixtures thereof. Next, pump the product from the blending section via a hose into a single nozzle, then place the nozzle into a container and fill the container with the resulting product. The stripe size is about 6 mm in width and 100 mm in length. The products remain stable at ambient for at least 180 days.

What is claimed is:

1. A rinse-off personal care composition comprising: a) from about 1% to about 95% by weight of a lipid phase, based on the total weight of said personal care composition, having a viscosity in the range of from about 100 to about 200,000 poise measured at 1 $Sec^{-1}$ according to the Lipid Rheology Method, said lipid phase comprising: i. no more than about 85%, by weight of said lipid phase, of a lipid; ii. a lipid structurant; iii. no more than about 70%, by weight of said personal care composition, of a hydrophilic liquid; iv. a structurant for said hydrophilic liquid; v. a surface active; wherein said hydrophilic liquid, said structurant for said hydrophilic liquid, and said surface active are on the surface of said lipid, within the domain of said lipid, or both on the surface and within the domain of said lipid in said lipid phase; and b) an aqueous phase; wherein said lipid phase is disposed within a domain of said aqueous phase; and wherein said hydrophilic liquid is deposited into skin and/or hair after said personal care composition is rinsed off of said skin and/or hair.

2. The personal care composition of claim 1, wherein said lipid is selected from the group consisting of petrolatum, mineral oil, ester lipids, silicone lipids, and mixtures thereof.

3. The personal care composition of claim 1, wherein said hydrophilic liquid is glycerin.

4. The personal care composition of claim 1 wherein said structurant for said hydrophilic liquid is selected from the group consisting of association structure forming materials, inorganic particulate thickeners, and water-soluble and water-swellable polymers.

5. The personal care composition of claim 1 wherein said structurant for said hydrophilic liquid is selected from the group consisting of inorganic particulate thickeners, and water-soluble and water-swellable polymers.

6. The personal care composition of claim 1 wherein said surface active comprises association structure forming materials.

7. The personal care composition of claim 6 wherein said association structure forming materials form association structures selected from the group consisting of micelles, reverse micelles, lyotropic liquid crystals, and mixtures thereof.

8. The personal care composition of claim 6 wherein said association structure forming materials are selected from the group consisting of anionic, cationic, nonionic, amphoteric surfactants, alkoxylated polymers, polysaccharides, silicone copolyols, and aminosilicones.

9. The personal care composition of claim 1 wherein said structurant for said hydrophilic liquid and said surface active are both association structure forming materials.

10. The personal care composition of claim 1 wherein the ratio of said structurant for said hydrophilic liquid to said hydrophilic liquid is from about 1:1000 to about 100:1.

11. The personal care composition of claim 1 wherein the ratio of said surface active to said hydrophilic liquid is from about 1:1000 to about 20:1.

12. The personal care composition of claim 1 wherein the combination of said hydrophilic liquid and said structurant for said hydrophilic liquid form a material having a viscosity of at least about 3000 cst at 25° C.

13. The personal care composition of claim 1 wherein said lipid structurant is a block copolymer.

14. The personal care composition of claim 1 further comprising an additional aqueous phase that is a visually distinct phase that is packaged in physical contact with said composition while maintaining stability.

15. The personal care composition of claim 14 wherein said additional aqueous phase further comprises a mixture of surfactants.

16. The personal care composition of claim 15 wherein said mixture of surfactants is selected from the group consisting of anionic surfactants, nonionic surfactants, cationic surfactants, amphoteric surfactants and mixtures thereof.

17. The personal care composition of claim 1 further comprising an emulsifier.

18. The personal care composition of claim 1 further comprising an optional ingredient selected from the group consisting of structurant for aqueous phase, surfactant, and cationic polymers.

19. The personal care composition of claim 1 wherein said composition deposits at least 1 μg/$cm^2$ of said hydrophilic liquid on skin according to the in-vivo deposition method when the concentration of said hydrophilic liquid is at 5.0% of said personal care composition.

20. A rinse-off personal care composition comprising: a) from about 1% to about 95% by weight of a lipid phase, based on the total weight of the personal care composition, having a viscosity in the range of from about 100 to about 200,000 poise measured at 1 $Sec^{-1}$ according to the Lipid Rheology Method, the lipid phase comprising: i. no more than about 85%, by weight of said lipid phase, of a lipid, wherein the lipid is a hydrocarbon; ii. a hydrophilic liquid/hydrophilic liquid structurant complex; iii. a surface active; wherein the hydrophilic liquid/hydrophilic liquid structurant complex and the surface active are on the surface of the lipid, within the domain of the lipid, or both on the surface and within the domain of the lipid in the lipid phase; and b) an aqueous phase comprising an aqueous phase polymeric structurant; wherein the lipid phase is disposed within a domain of the aqueous phase; and wherein the hydrophilic liquid is deposited into skin and/or hair after the personal care composition is rinsed off of the skin and/or hair.

* * * * *

UNITED STATES PATENT AND TRADEMARK OFFICE
CERTIFICATE OF CORRECTION

| | | |
|---|---|---|
| PATENT NO. | : 8,263,058 B2 | Page 1 of 1 |
| APPLICATION NO. | : 11/894142 | |
| DATED | : September 11, 2012 | |
| INVENTOR(S) | : Qing Stella et al. | |

It is certified that error appears in the above-identified patent and that said Letters Patent is hereby corrected as shown below:

In the Claims

Column 31, Line 49
Claim 1(b) delete "into", insert --onto--.

Column 32, Line 63
Claim 20(b) delete "into", insert --onto--.

Signed and Sealed this
Twenty-eighth Day of April, 2015

Michelle K. Lee
*Director of the United States Patent and Trademark Office*